United States Patent
Coles et al.

(10) Patent No.: US 9,101,745 B2
(45) Date of Patent: Aug. 11, 2015

(54) SONOCHEMICAL INDUCTION OF ABCA1 EXPRESSION AND COMPOSITIONS THEREFOR

(71) Applicant: SONOGENE, LLC, Glen Ellyn, IL (US)

(72) Inventors: Eric Coles, Glen Ellyn, IL (US); Michael Davidson, Highland Park, IL (US)

(73) Assignee: SONOGENE LLC, Glen Ellyn, IL (US)

( * ) Notice: Subject to any disclaimer, the term of this patent is extended or adjusted under 35 U.S.C. 154(b) by 62 days.

(21) Appl. No.: 13/826,066

(22) Filed: Mar. 14, 2013

(65) Prior Publication Data
US 2014/0276363 A1    Sep. 18, 2014

(51) Int. Cl.
| | | |
|---|---|---|
| A61M 37/00 | (2006.01) | |
| A61K 31/7088 | (2006.01) | |
| A61K 45/06 | (2006.01) | |
| A61K 49/22 | (2006.01) | |
| A61K 41/00 | (2006.01) | |
| A61K 48/00 | (2006.01) | |
| A61K 31/713 | (2006.01) | |
| C12N 15/00 | (2006.01) | |

(52) U.S. Cl.
CPC ........ *A61M 37/0092* (2013.01); *A61K 31/7088* (2013.01); *A61K 31/713* (2013.01); *A61K 41/0028* (2013.01); *A61K 45/06* (2013.01); *A61K 48/00* (2013.01); *C12N 15/00* (2013.01)

(58) Field of Classification Search
CPC ........................ A61K 41/0028; A61M 37/0092
See application file for complete search history.

(56) References Cited

U.S. PATENT DOCUMENTS

| | | | |
|---|---|---|---|
| 5,190,766 | A | 3/1993 | Ishihara et al. |
| 5,498,421 | A | 3/1996 | Grinstaff et al. |
| 5,542,935 | A | 8/1996 | Unger et al. |
| 5,558,092 | A | 9/1996 | Unger et al. |
| 5,580,575 | A | 12/1996 | Unger et al. |
| 5,770,222 | A | 6/1998 | Unger et al. |
| 5,849,727 | A | 12/1998 | Porter et al. |
| 5,961,459 | A | 10/1999 | Kaul et al. |
| 6,048,903 | A | 4/2000 | Toppo |
| 6,066,123 | A | 5/2000 | Li et al. |
| 6,068,857 | A | 5/2000 | Weitschies et al. |
| 6,071,495 | A | 6/2000 | Unger et al. |
| 6,117,858 | A | 9/2000 | Porter et al. |
| 6,120,751 | A | 9/2000 | Unger |
| RE36,939 | E | 10/2000 | Tachibana et al. |
| 6,135,976 | A | 10/2000 | Tachibana et al. |
| 6,139,819 | A | 10/2000 | Unger et al. |
| 6,265,387 | B1 | 7/2001 | Wolff et al. |
| 6,575,956 | B1 | 6/2003 | Brisken et al. |
| 7,211,248 | B2 * | 5/2007 | Davidson ................ 424/93.2 |
| 7,351,535 | B2 | 4/2008 | Lawn et al. |
| 2001/0008758 | A1 | 7/2001 | McHale et al. |
| 2001/0009904 | A1 | 7/2001 | Wolff et al. |
| 2002/0165191 | A1 | 11/2002 | Moonen |
| 2004/0266663 | A1 | 12/2004 | Schwartz et al. |

FOREIGN PATENT DOCUMENTS

| | | |
|---|---|---|
| CN | 1056124 | 11/1995 |
| WO | 0042988 A1 | 7/2000 |

OTHER PUBLICATIONS

Vaisman et al. (J. Clin. Invest. 2001; 1008: 303-309).*
Attie, A.D. et al., Pivotal Role of ABCA1 in Reverse Cholesterol Transport Influencing HDL Levels and Susceptibility to Atherosclerosis, Journal of Lipid Research, vol. 42, 1717-1726 (2001).
Dong, C. et al., ABCA1 Single Nucleotide Polymorphisms: Snipping at the Pathogenesis of Atherosclerosis, Circulation Research, vol. 88, 855-857 (2001).
Oram, J.F. et al., ATP-Binding Cassette Cholesterol Transporters and Cardiovascular Disease, Circulation Research, vol. 99, 1031-1043 (2006).
Shohet, R.V. et al., Echocardiographic Destruction of Albumin Microbubbles Directs Gene Delivery to the Myocardium, Circulation, vol. 101, 2554-2556 (2000).
Zarubica, A. et al., Functional Implications of the Influence of ABCA1 on Lipid Microenvironment at the Plasma Membrane: a Biophysical Study, The FASEB Journal, vol. 23, 1775-1785 (2009).
Trompier, D. et al., Transition from Dimers to Higher Oligomeric Forms Occurs During the ATPase Cycle of the ABCA1 Transporter, Journal of Biological Chemistry, vol. 281, No. 29, 20283-20290 (2006).
He, Y. et al., Ultrasound Microbubble-Mediated Delivery of the siRNAs Targeting MDR1 Reduces Drug Resistance of Yolk Sac Carcinoma L2 Cells, Journal of Experimental & Clinical Cancer Research, vol. 30:104, 1-11 (2011).
Dijkmans, P.A. et al., Microbubbles and Ultrasound: From Diagnosis to Therapy, Eur. J. Echocardiography, vol. 5, 245-256 (2004).
Lawrie, A. et al., Microbubble-Enhanced Ultrasound for Vascular Gene Delivery, Gene Therapy, vol. 7, 2023-2027 (2000).
Kaufman, R.J., Overview of Vector Design for Mammalian Gene Expression, Molecular Biotechnology, vol. 16, 151-160 (2000).
Smith, B., et al., Anticancer Activity of the Cholesterol Exporter ABCA1 Gene, Cell Reports 2, 580-590 (2012).

(Continued)

*Primary Examiner* — Scott Long
(74) *Attorney, Agent, or Firm* — Olson & Cepuritis, Ltd.

(57) ABSTRACT

The present invention provides compositions useful for transfecting cells (e.g., liver cells) to express ABCA1. The compositions described herein comprise a pharmaceutically acceptable aqueous carrier containing sonochemically-active microspheres together with a plasmid DNA construct encoding an active form of ABCA1 and at least one promoter for the expression thereof. Preferably, the sonochemically-active microspheres comprise, consist essentially of, or consist of gas bubbles (e.g., a fluorocarbon gas, such as octafluoropropane) encapsulated within protein-containing or lipid-containing shells (e.g., human serum albumin shells). The microspheres are disruptable by exposure to ultrasonic acoustic energy to release the encapsulated gas.

14 Claims, 11 Drawing Sheets

(56) References Cited

OTHER PUBLICATIONS

Duong, P.T. et al., Characterization and Properties of Preβ-HDL Particles Formed by ABCA1-Mediated Cellular Lipid Efflux to ApoA-1, J. Lipid Res. vol. 49(5), 1006-1014 (2008).
Iatan, I. et al., Effect of ABCA1 Mutations on Risk for Myocardial Infarction, Clinical Trials and Their Interpretations, Current Atherosclerosis Reports, vol. 10, 413-426 (2008).
Oram, J.F. et al., ATP-Binding Cassette Transporter A1: A Cell Cholesterol Exporter that Protects Against Cardiovascular Disease, Physiol. Rev. vol. 85, 1343-1372 (2005).
Ohashi R. et al., Reverse Cholesterol Transport and Cholesterol Efflux in Atherosclerosis, QJ Med vol. 98, 845-856 (2005).
Sporstol, M. et al., ABCA1, ABCGI and SR-BI: Hormonal Regulation in Primary Rat Hepatocytes and Human Cell Lines, BMC Molecular Biology vol. 8 (5), 1-8 (2007).
Yang, Y. et al., Suppression of ABCA1 by Unsaturated Fatty Acids Leads to Lipid Accumulation in HepG2 Cells, Biochimie vol. 92, 958-963 (2010).
Liao, H. et al., Native LDL Upregulation of ATP-Binding Cassette Transporter-1 in Human Vascular Endothelial Cells, Arteriosclerosis, Thrombosis, and Vascular Biology, vol. 22, 127-132 (2002).
GenBank: OriGene TrueORF Data, *Homo sapiens* ATP-Binding Cassette, Sub-family A (ABC1) Member 1 (ABCA1), mRNA, NCBI Reference Sequence NM_005502.2.
Skyba, D.M. et al., Direct In Vivo Visualization of Intravascular Destruction of Microbubbles by Ultrasound and Its Local Effects on Tissue, Circulation vol. 98, 290-293 (1998).
Klibanov, A.L. et al., Targeted Delivery of Gas-Filled Microspheres, Contrast Agents for Ultrasound Imaging, Advanced Drug Delivery Reviews, vol. 37, 139-157 (1999).
Miller, D.L. et al., Ultrasonic Enhancement of Gene Transfection in Murine Melanoma Tumors, Ultrasound in Medicine & Biology, vol. 25 (9), 1425-1430 (1999).
Kim, H.J. et al., Ultrasound-Mediated Transfection of Mammalian Cells, Human Gene Therapy vol. 7, 1339-1346 (1996).
Lawrie, A. et al., Ultrasound-Enhanced Transgene Expression in Vascular Cells is Not Dependent Upon Cavitation-Induced Free Radicals, Ultrasound in Med. & Biol., vol. 29 (10), 1453-1461 (2003).
Shohet et al., Microbubbles Used to "Pop" New Gene Into the Heart, Clinical Genetics, vol. 58(4), 269 (2000).
Manome, Y. et al., Ultrasound Facilitates Transduction of Naked Plasmid DNA into Colon Carcinoma Cells in Vitro and in Vivo, Human Gene Therapy, vol. 11, 1521-1528 (2000).
Anwer, K. et al., Ultrasound Enhancement of Cationic Lipid-Mediated Gene Transfer to Primary Tumors Following Systemic Administration, Gene Therapy, vol. 7, 1833-1839 (2000).
Tangirala, R.K. et al., Regression of Atherosclerosis Induced by Liver Directed Gene Transfer of Apolipoprotein A-I in Mice, Circulation, vol. 100, 1816-1822 (1999).
Dansky, H.M. et al., High-Density Lipoprotein and Plaque Regression, The Good Cholesterol Gets Even Better, Circulation, vol. 100, 1762-1763 (1999).
Tsukamoto, K. et al., Comparison of Human ApoA-1 Expression in Mouse Models of Atherosclerosis After Gene Transfer Using a Second Generation Adenovirus, Journal of Lipid Research, vol. 38, 1869-1876 (1997).
Boisvert, W.A. et al., ApoA1 Reduces Free Cholesterol Accumulation in Atherosclerotic Lesions of ApoE-Deficient Mice Transplanted with ApoE-Expressing Macrophages, Arterioscler Thromb Vasc. Biol. vol. 19, 525-530 (1999).
Huber, P.E. et al., In Vitro and In Vivo Transfection of Plasmid DNA in the Dunning Prostate Tumor R3327-AT1 is Enhanced by Focused Ultrasound, Gene Therapy, vol. 7, 1516-1525 (2000).
Lawrie, A. et al., Ultrasound Enhances Reporter Gene Expression After Transfection of Vascular Cells in Vitro, Circulation, vol. 99, 2617-2620 (1999).
Dass C. et al., Apolipoprotein A-1, Phospholipid Vesicles and Cyclodextrins as Potential Anti-Atherosclerotic Drugs: Delivery, Pharmacokinetics, and Efficacy, vol. 7, 161-182 (2000).
Nanjee, M.N. et al., Acute Effects of Intravenous Infusion of ApoA1/Phosphatidylcholine Discs on Plasma Lipoproteins in Humans, Arterioscler Thromb Vasc. Biol., vol. 19, 979-989 (1999).
Chomas, J.E. et al., Threshold of Fragmentation for Ultrasonic Contrast Agents, Journal of Biomedical Optics, vol. 6 (2), 141-150 (2001).
Fechheimer, M. et al., Transfection of Mammalian Cells with Plasmid DNA by Scrape Loading and Sonication Loading, Proc. Natl. Acad. Sci., vol. 84, 8463-8467 (1987).
Product Insert for OPTISON Ultrasound Contrast Agent, "OPTISON" (Perflutren Protein—Type A Microspheres for Injection, USP, revised Jun. 2003.
Reznik, N. et al., On the Acoustic Properties of Vaporized Submicron Perfluorocarbon Droplets, Ultrasound in Med. & Biol., vol. 40 (6), 1379-1384 (2014).
Sun, D. et al., MiR-26 Controls LXR-dependent Cholesterol Efflux by Targeting ABCA1 and ARL7, FEBS Letters 586, 1472-1479 (2012).
Panje, C.M. et al., Ultrasound-Mediated Gene Delivery with Cationic Versus Neutral Microbubbles: Effect of DNA and Microbubble Dose on In Vivo Transfection Efficiency, Theranostics 2 (11), 1078-1091 (2012).
Takahashi, M. et al., Spinal Gene Transfer Using Ultrasound and Microbubbles, Journal of Controlled Release 117, 267-272 (2007).
Hernot, S. et al., Microbubbles in Ultrasound-Triggered Drug and Gene Delivery, Advanced Drug Delivery Reviews 60, 1153-1166 (2008).
Guo, D.-P. et al., Ultrasound-Targeted Microbubble Destruction Improves the Low Density Lipoprotein Receptor Gene Expression in HepG2 Cells, Biochemical and Biophysical Research Communications 343, 470-474 (2006).

* cited by examiner

(SEQ ID NO: 1):

```
MACWPQLRLLLWKNLTFRRRQTCQLLLEVAWPLFIFLILISVRLSYPPYEQHECHFPNKA
MPSAGTLPWVQGIICNANNPCFRYPTPGEAPGVVGNFNKSIVARLFSDARRLLLYSQKDT
SMKDMRKVLRTLQQIKKSSSNLKLQDFLVDNETFSGFLYHNLSLPKSTVDKMLRADVILH
KVFLQGYQLHLTSLCNGSKSEEMIQLGDQEVSELCGLPREKLAAAERVLRSNMDILKPIL
RTLNSTSPFPSKELAEATKTLLHSLGTLAQELFSMRSWSDMRQEVMFLTNVNSSSSSTQI
YQAVSRIVCGHPEGGGLKIKSLNWYEDNNYKALFGGNGTEEDAETFYDNSTTPYCNDLMK
NLESSPLSRIIWKALKPLLVGKILYTPDTPATRQVMAEVNKTFQELAVFHDLEGMWEELS
PKIWTFMENSQEMDLVRMLLDSRDNDHFWEQQLDGLDWTAQDIVAFLAKHPEDVQSSNGS
VYTWREAFNETNQAIRTISRFMECVNLNKLEPIATEVWLINKSMELLDERKFWAGIVFTG
ITPGSIELPHHVKYKIRMDIDNVERTNKIKDGYWDPGPRADPFEDMRYVWGGFAYLQDVV
EQAIIRVLTGTEKKTGVYMQQMPYPCYVDDIFLRVMSRSMPLFMTLAWIYSVAVIIKGIV
YEKEARLKETMRIMGLDNSILWFSWFISSLIPLLVSAGLLVVILKLGNLLPYSDPSVVFV
FLSVFAVVTILQCFLISTLFSRANLAAACGGIIYFTLYLPYVLCVAWQDYVGFTLKIFAS
LLSPVAFGFGCEYFALFEEQGIGVQWDNLFESPVEEDGFNLTTSVSMMLFDTFLYGVMTW
YIEAVFPGQYGIPRPWYFPCTKSYWFGEESDEKSHPGSNQKRISEICMEEEPTHLKLGVS
IQNLVKVYRDGMKVAVDGLALNFYEGQITSFLGHNGAGKTTTMSILTGLFPPTSGTAYIL
GKDIRSEMSTIRQNLGVCPQHNVLFDMLTVEEHIWFYARLKGLSEKHVKAEMEQMALDVG
LPSSKLKSKTSQLSGGMQRKLSVALAFVGGSKVVILDEPTAGVDPYSRRGIWELLLKYRQ
GRTIILSTHHMDEADVLGDRIAIISHGKLCCVGSSLFLKNQLGTGYYLTLVKKDVESSLS
SCRNSSSTVSYLKKEDSVSQSSSDAGLGSDHESDTLTIDVSAISNLIRKHVSEARLVEDI
GHELTYVLPYEAAKEGAFVELFHEIDDRLSDLGISSYGISETTLEEIFLKVAEESGVDAE
TSDGTLPARRNRRAFGDKQSCLRPFTEDDAADPNDSDIDPESRETDLLSGMDGKGSYQVK
GWKLTQQQFVALLWKRLLIARRSRKGFFAQIVLPAVFVCIALVFSLIVPPFGKYPSLELQ
PWMYNEQYTFVSNDAPEDTGTLELLNALTKDPGFGTRCMEGNPIPDTPCQAGEEEWTTAP
VPQTIMDLFQNGNWTMQNPSPACQCSSDKIKKMLPVCPPGAGGLPPPQRKQNTADILQDL
TGRNISDYLVKTYVQIIAKSLKNKIWVNEFRYGGFSLGVSNTQALPPSQEVNDAIKQMKK
HLKLAKDSSADRFLNSLGRFMTGLDTKNNVKVWFNNKGWHAISSFLNVINNAILRANLQK
GENPSHYGITAFNHPLNLTKQQLSEVALMTTSVDVLVSICVIFAMSFVPASFVVFLIQER
VSKAKHLQFISGVKPVIYWLSNFVWDMCNYVVPATLVIIIFICFQQKSYVSSTNLPVLAL
LLLLYGWSITPLMYPASFVFKIPSTAYVVLTSVNLFIGINGSVATFVLELFTDNKLNNIN
DILKSVFLIFPHFCLGRGLIDMVKNQAMADALERFGENRFVSPLSWDLVGRNLFAMAVEG
VVFFLITVLIQYRFFIRPRPVNAKLSPLNDEDEDVRRERQRILDGGGQNDILEIKELTKI
YRRKRKPAVDRICVGIPPGECFGLLGVNGAGKSSTFKMLTGDTTVTRGDAFLNKNSILSN
IHEVHQNMGYCPQFDAITELLTGREHVEFFALLRGVPEKEVGKVGEWAIRKLGLVKYGEK
YAGNYSGGNKRKLSTAMALIGGPPVVFLDEPTTGMDPKARRFLWNCALSVVKEGRSVVLT
SHSMEECEALCTRMAIMVNGRFRCLGSVQHLKNRFGDGYTIVVRIAGSNPDLKPVQDFFG
LAFPGSVLKEKHRNMLQYQLPSSLSSLARIFSILSQSKKRLHIEDYSVSQTTLDQVFVNF
AKDQSDDDHLKDLSLHKNQTVVDVAVLTSFLQDEKVKESYV
```

FIG. 1

(SEQ ID NO: 2):

```
ATGGCTTGTTGGCCTCAGCTGAGGTTGCTGCTGTGGAAGAACCTCACTTTCAGAAGAAGACAAAC
ATGTCAGCTGCTGCTGGAAGTGGCCTGGCCTCTATTTATCTTCCTGATCCTGATCTCTGTTCGGC
TGAGCTACCCACCCTATGAACAACATGAATGCCATTTTCCAAATAAAGCCATGCCCTCTGCAGGA
ACACTTCCTTGGGTTCAGGGGATTATCTGTAATGCCAACAACCCCTGTTTCCGTTACCCGACTCC
TGGGGAGGCTCCCGGAGTTGTTGGAAACTTTAACAAATCCATTGTGGCTCGCCTGTTCTCAGATG
CTCGGAGGCTTCTTTTATACAGCCAGAAAGACACCAGCATGAAGGACATGCGCAAAGTTCTGAGA
ACATTACAGCAGATCAAGAAATCCAGCTCAAACTTGAAGCTTCAAGATTTCCTGGTGGACAATGA
AACCTTCTCTGGGTTCCTGTATCACAACCTCTCTCTCCCAAAGTCTACTGTGGACAAGATGCTGA
GGGCTGATGTCATTCTCCACAAGGTATTTTTGCAAGGCTACCAGTTACATTTGACAAGTCTGTGC
AATGGATCAAAATCAGAAGAGATGATTCAACTTGGTGACCAAGAAGTTTCTGAGCTTTGTGGCCT
ACCAAGGGAGAAACTGGCTGCAGCAGAGCGAGTACTTCGTTCCAACATGGACATCCTGAAGCCAA
TCCTGAGAACACTAAACTCTACATCTCCCTTCCCGAGCAAGGAGCTGGCTGAAGCCACAAAAACA
TTGCTGCATAGTCTTGGGACTCTGGCCCAGGAGCTGTTCAGCATGAGAAGCTGGAGTGACATGCG
ACAGGAGGTGATGTTTCTGACCAATGTGAACAGCTCCAGCTCCTCCACCCAAATCTACCAGGCTG
TGTCTCGTATTGTCTGCGGGCATCCCGAGGGAGGGGGGCTGAAGATCAAGTCTCTCAACTGGTAT
GAGGACAACAACTACAAAGCCCTCTTTGGAGGCAATGGCACTGAGGAAGATGCTGAAACCTTCTA
TGACAACTCTACAACTCCTTACTGCAATGATTTGATGAAGAATTTGGAGTCTAGTCCTCTTTCCC
GCATTATCTGGAAAGCTCTGAAGCCGCTGCTCGTTGGGAAGATCCTGTATACACCTGACACTCCA
GCCACAAGGCAGGTCATGGCTGAGGTGAACAAGACCTTCCAGGAACTGGCTGTGTTCCATGATCT
GGAAGGCATGTGGGAGGAACTCAGCCCCAAGATCTGGACCTTCATGGAGAACAGCCAAGAAATGG
ACCTTGTCCGGATGCTGTTGGACAGCAGGGACAATGACCACTTTGGGAACAGCAGTTGGATGGC
TTAGATTGGACAGCCCAAGACATCGTGGCGTTTTTGGCCAAGCACCCAGAGGATGTCCAGTCCAG
TAATGGTTCTGTGTACACCTGGAGAGAAGCTTTCAACGAGACTAACCAGGCAATCCGGACCATAT
CTCGCTTCATGGAGTGTGTCAACCTGAACAAGCTAGAACCCATAGCAACAGAAGTCTGGCTCATC
AACAAGTCCATGGAGCTGCTGGATGAGAGGAAGTTCTGGGCTGGTATTGTGTTCACTGGAATTAC
TCCAGGCAGCATTGAGCTGCCCCATCATGTCAAGTACAAGATCCGAATGGACATTGACAATGTGG
AGAGGACAAATAAAATCAAGGATGGGTACTGGGACCCTGGTCCTCGAGCTGACCCCTTTGAGGAC
ATGCGGTACGTCTGGGGGGCTTCGCCTACTTGCAGGATGTGGTGGAGCAGGCAATCATCAGGGT
GCTGACGGGCACCGAGAAGAAAACTGGTGTCTATATGCAACAGATGCCCTATCCCTGTTACGTTG
ATGACATCTTTCTGCGGGTGATGAGCCGGTCAATGCCCCTCTTCATGACGCTGGCCTGGATTTAC
TCAGTGGCTGTGATCATCAAGGGCATCGTGTATGAAGGAGGCACGGCTGAAAGAGACCATGCG
GATCATGGGCCTGGACAACAGCATCCTCTGGTTTAGCTGGTTCATTAGTAGCCTCATTCCTCTTC
TTGTGAGCGCTGGCCTGCTAGTGGTCATCCTGAAGTTAGGAAACCTGCTGCCCTACAGTGATCCC
AGCGTGGTGTTTGTCTTCCTGTCCGTGTTTGCTGTGGTGACAATCCTGCAGTGCTTCCTGATTAG
CACACTCTTCTCCAGAGCCAACCTGGCAGCAGCCTGTGGGGCATCATCTACTTCACGCTGTACC
TGCCCTACGTCCTGTGTGTGGCATGGCAGGACTACGTGGGCTTCACACTCAAGATCTTCGCTAGC
CTGCTGTCTCCTGTGGCTTTTGGGTTTGCTGTGAGTACTTTGCCCTTTTTGAGGAGCAGGGCAT
TGGAGTGCAGTGGGACAACCTGTTTGAGAGTCCTGTGGAGGAAGATGGCTTCAATCTCACCACTT
```

FIG. 2

```
CGGTCTCCATGATGCTGTTTGACACCTTCCTCTATGGGGTGATGACCTGGTACATTGAGGCTGTC
TTTCCAGGCCAGTACGGAATTCCCAGGCCCTGGTATTTTCCTTGCACCAAGTCCTACTGGTTTGG
CGAGGAAAGTGATGAGAAGAGCCACCCTGGTTCCAACCAGAAGAGAATATCAGAAATCTGCATGG
AGGAGGAACCCACCCACTTGAAGCTGGGCGTGTCCATTCAGAACCTGGTAAAAGTCTACCGAGAT
GGGATGAAGGTGGCTGTCGATGGCCTGGCACTGAATTTTATGAGGGCCAGATCACCTCCTTCCT
GGGCCACAATGGAGCGGGGAAGACGACCACCATGTCAATCCTGACCGGGTTGTTCCCCCCGACCT
CGGGCACCGCCTACATCCTGGGAAAAGACATTCGCTCTGAGATGAGCACCATCCGGCAGAACCTG
GGGGTCTGTCCCCAGCATAACGTGCTGTTTGACATGCTGACTGTCGAAGAACACATCTGGTTCTA
TGCCCGCTTGAAAGGGCTCTCTGAGAAGCACGTGAAGGCGGAGATGGAGCAGATGGCCCTGGATG
TTGGTTTGCCATCAAGCAAGCTGAAAAGCAAAACAAGCCAGCTGTCAGGTGGAATGCAGAGAAAG
CTATCTGTGGCCTTGGCCTTTGTCGGGGATCTAAGGTTGTCATTCTGGATGAACCCACAGCTGG
TGTGGACCCTTACTCCCGCAGGGGAATATGGGAGCTGCTGCTGAAATACCGACAAGGCCGCACCA
TTATTCTCTACACCACATGGATGAAGCGGACGTCCTGGGGGACAGGATTGCCATCATCTCC
CATGGGAAGCTGTGCTGTGTGGGCTCCTCCCTGTTTCTGAAGAACCAGCTGGGAACAGGCTACTA
CCTGACCTTGGTCAAGAAAGATGTGGAATCCTCCCTCAGTTCCTGCAGAAACAGTAGTAGCACTG
TGTCATACCTGAAAAAGGAGGACAGTGTTTCTCAGAGCAGTTCTGATGCTGGCCTGGGCAGCGAC
CATGAGAGTGACACGCTGACCATCGATGTCTCTGCTATCTCCAACCTCATCAGGAAGCATGTGTC
TGAAGCCCGGCTGGTGGAAGACATAGGGCATGAGCTGACCTATGTGCTGCCATATGAAGCTGCTA
AGGAGGGAGCCTTTGTGGAACTCTTTCATGAGATTGATGACCGGCTCTCAGACCTGGGCATTTCT
AGTTATGGCATCTCAGAGACGACCCTGGAAGAAATATTCCTCAAGGTGGCCGAAGAGAGTGGGGT
GGATGCTGAGACCTCAGATGGTACCTTGCCAGCAAGACGAAACAGGCGGGCCTTCGGGGACAAGC
AGAGCTGTCTTCGCCCGTTCACTGAAGATGATGCTGCTGATCCAAATGATTCTGACATAGACCCA
GAATCCAGAGAGACAGACTTGCTCAGTGGGATGGATGGCAAAGGGTCCTACCAGGTGAAAGGCTG
GAAACTTACACAGCAACAGTTTGTGGCCCTTTTGTGGAAGAGACTGCTAATTGCCAGACGGAGTC
GGAAAGGATTTTTTGCTCAGATTGTCTTGCCAGCTGTGTTTGTCTGCATTGCCCTTGTGTTCAGC
CTGATCGTGCCACCCTTTGGCAAGTACCCCAGCCTGGAACTTCAGCCCTGGATGTACAACGAACA
GTACACATTTGTCAGCAATGATGCTCCTGAGGACACGGGAACCCTGGAACTCTTAAACGCCCTCA
CCAAAGACCCTGGCTTCGGGACCCGCTGTATGGAAGGAAACCCAATCCCAGACACGCCCTGCCAG
GCAGGGAGGAAGAGTGGACCACTGCCCCAGTTCCCCAGACCATCATGGACCTCTTCCAGAATGG
GAACTGGACAATGCAGAACCCTTCACCTGCATGCCAGTGTAGCAGCGACAAAATCAAGAAGATGC
TGCCTGTGTGTCCCCCAGGGGCAGGGGGCTGCCTCCTCCACAAAGAAAACAAAACACTGCAGAT
ATCCTTCAGGACCTGACAGGAAGAAACATTTCGGATTATCTGGTGAAGACGTATGTGCAGATCAT
AGCCAAAAGCTTAAAGAACAAGATCTGGGTGAATGAGTTTAGGTATGGCGGCTTTTCCCTGGGTG
TCAGTAATACTCAAGCACTTCCTCCGAGTCAAGAAGTTAATGATGCCATCAAACAAATGAAGAAA
CACCTAAAGCTGGCCAAGGACAGTTCTGCAGATCGATTTCTCAACAGCTTGGGAAGATTTATGAC
AGGACTGGACACCAAAAATAATGTCAAGGTGTGGTTCAATAACAAGGGCTGGCATGCAATCAGCT
CTTTCCTGAATGTCATCAACAATGCCATTCTCCGGGCCAACCTGCAAAAGGGAGAGAACCCTAGC
CATTATGGAATTACTGCTTTCAATCATCCCCTGAATCTCACCAAGCAGCAGCTCTCAGAGGTGGC
TCTGATGACCACATCAGTGGATGTCCTTGTGTCCATCTGTGTCATCTTTGCAATGTCCTTCGTCC
CAGCCAGCTTTGTCGTATTCCTGATCCAGGAGCGGGTCAGCAAAGCAAAACACCTGCAGTTCATC
AGTGGAGTGAAGCCTGTCATCTACTGGCTCTCTAATTTTGTCTGGGATATGTGCAATTACGTTGT
```

FIG. 2 (cont.)

```
CCCTGCCACACTGGTCATTATCATCTTCATCTGCTTCCAGCAGAAGTCCTATGTGTCCTCCACCA
ATCTGCCTGTGCTAGCCCTTCTACTTTTGCTGTATGGGTGGTCAATCACACCTCTCATGTACCCA
GCCTCCTTTGTGTTCAAGATCCCCAGCACAGCCTATGTGGTGCTCACCAGCGTGAACCTCTTCAT
TGGCATTAATGGCAGCGTGGCCACCTTTGTGCTGGAGCTGTTCACCGACAATAAGCTGAATAATA
TCAATGATATCCTGAAGTCCGTGTTCTTGATCTTCCCACATTTTTGCCTGGGACGAGGGCTCATC
GACATGGTGAAAAACCAGGCAATGGCTGATGCCCTGGAAAGGTTTGGGGAGAATCGCTTTGTGTC
ACCATTATCTTGGGACTTGGTGGGACGAAACCTCTTCGCCATGGCCGTGGAAGGGGTGGTGTTCT
TCCTCATTACTGTTCTGATCCAGTACAGATTCTTCATCAGGCCCAGACCTGTAAATGCAAAGCTA
TCTCCTCTGAATGATGAAGATGAAGATGTGAGGCGGGAAAGACAGAGAATTCTTGATGGTGGAGG
CCAGAATGACATCTTAGAAATCAAGGAGTTGACGAAGATATATAGAAGGAAGCGGAAGCCTGCTG
TTGCACAGGATTTGCGTGGGCATTCCTCCTGGTGAGTGCTTTGGGCTCCTGGGAGTTAATGGGGCT
GGAAAATCATCAACTTTCAAGATGTTAACAGGAGATACCACTGTTACCAGAGGAGATGCTTTCCT
TAACAAAAATAGTATCTTATCAAACATCCATGAAGTACATCAGAACATGGGCTACTGCCCTCAGT
TTGATGCCATCACAGAGCTGTTGACTGGGAGAGAACACGTGGAGTTCTTTGCCCTTTTGAGAGGA
GTCCCAGAGAAAGAAGTTGGCAAGGTTGGTGAGTGGGCGATTCGGAAACTGGGCCTCGTGAAGTA
TGGAGAAAAATATGCTGGTAACTATAGTGGAGGCAACAAACGCAAGCTCTCTACAGCCATGGCTT
TGATCGGCGGGCCTCCTGTGGTGTTTCTGGATGAACCCACCACAGGCATGGATCCCAAAGCCCGG
CGGTTCTTGTGGAATTGTGCCCTAAGTGTTGTCAAGGAGGGGAGATCAGTAGTGCTTACATCTCA
TAGTATGGAAGAATGTGAAGCTCTTTGCACTAGGATGGCAATCATGGTCAATGGAAGGTTCAGGT
GCCTTGGCAGTGTCCAGCATCTAAAAAATAGGTTTGGAGATGGTTATACAATAGTTGTACGAATA
GCAGGGTCCAACCCGGACCTGAAGCCTGTCCAGGATTTCTTTGGACTTGCATTTCCTGGAAGTGT
TCTAAAAGAGAAACACCGGAACATGCTACAATACCAGCTTCCATCTTCATTATCTTCTCTGGCCA
GGATATTCAGCATCCTCTCCCAGAGCAAAAAGCGACTCCACATAGAAGACTACTCTGTTTCTCAG
ACAACACTTGACCAAGTATTTGTGAACTTTGCCAAGGACCAAAGTGATGATGACCACTTAAAAGA
CCTCTCATTACACAAAAACCAGACAGTAGTGGACGTTGCAGTTCTCACATCTTTTCTACAGGATG
AGAAAGTGAAAGAAAGCTATGTA
```

FIG. 2 (cont.)

(SEQ ID NO: 3):

```
AACAAAATATTAACGCTTACAATTTCCATTCGCCATTCAGGCTGCGCAACTGTTGGGAAGGGCGA
TCGGTGCGGGCCTCTTCGCTATTACGCCAGCTGGCGAAAGGGGGATGTGCTGCAAGGCGATTAAG
TTGGGTAACGCCAGGGTTTTCCCAGTCACGACGTTGTAAAACGACGGCCAGTGCCAAGCTGATCT
ATACATTGAATCAATATTGGCAATTAGCCATATTAGTCATTGGTTATATAGCATAAATCAATATT
GGCTATTGGCCATTGCATACGTTGTATCTATATCATAATATGTACATTTATATTGGCTCATGTCC
AATATGACCGCCATGTTGACATTGATTATTGACTAGTTATTAATAGTAATCAATTACGGGGTCAT
TAGTTCATAGCCCATATATGGAGTTCCGCGTTACATAACTTACGGTAAATGGCCCGCCTGGCTGA
CCGCCCAACGACCCCGCCCATTGACGTCAATAATGACGTATGTTCCCATAGTAACGCCAATAGG
GACTTTCCATTGACGTCAATGGGTGGAGTATTTACGGTAAACTGCCCACTTGGCAGTACATCAAG
TGTATCATATGCCAAGTCCGCCCCCTATTGACGTCAATGACGGTAAATGGCCCGCCTGGCATTAT
GCCCAGTACATGACCTTACGGGACTTTCCTACTTGGCAGTACATCTACGTATTAGTCATCGCTAT
TACCATGGTGATGCGGTTTTGGCAGTACACCAATGGGCGTGGATAGCGGTTTGACTCACGGGGAT
TTCCAAGTCTCCACCCCATTGACGTCAATGGGAGTTTGTTTTGGCACCAAAATCAACGGGACTTT
CCAAAATGTCGTAATAACCCCGCCCCGTTGACGCAAATGGGCGGTAGGCGTGTACGGTGGGAGGT
CTATATAAGCAGAGCTCGTTTAGTGAACCGTCAGAATTTTGTAATACGACTCACTATAGGGCGGC
CGGGAATTCGTCGACTGGATCCGGTACCGAGGAGATCTGCCGCCGCGATCGCCATGGCTTGTTGG
CCTCAGCTGAGGTTGCTGCTGTGGAAGAACCTCACTTTCAGAAGAAGACAAACATGTCAGCTGCT
GCTGGAAGTGGCCTGGCCTCTATTTATCTTCCTGATCCTGATCTCTGTTCGGCTGAGCTACCCAC
CCTATGAACAACATGAATGCCATTTTCCAAATAAAGCCATGCCCTCTGCAGGAACACTTCCTTGG
GTTCAGGGGATTATCTGTAATGCCAACAACCCCTGTTTCCGTTACCCGACTCCTGGGGAGGCTCC
CGGAGTTGTTGGAAACTTTAACAAATCCATTGTGGCTCGCCTGTTCTCAGATGCTCGGAGGCTTC
TTTTATACAGCCAGAAAGACACCAGCATGAAGGACATGCGCAAAGTTCTGAGAACATTACAGCAG
ATCAAGAAATCCAGCTCAAACTTGAAGCTTCAAGATTTCCTGGTGGACAATGAAACCTTCTCTGG
GTTCCTGTATCACAACCTCTCTCTCCCAAAGTCTACTGTGGACAAGATGCTGAGGGCTGATGTCA
TTCTCCACAAGGTATTTTTGCAAGGCTACCAGTTACATTTGACAAGTCTGTGCAATGGATCAAAA
TCAGAAGAGATGATTCAACTTGGTGACCAAGAAGTTTCTGAGCTTTGTGGCCTACCAAGGGAGAA
ACTGGCTGCAGCAGAGCGAGTACTTCGTTCCAACATGGACATCCTGAAGCCAATCCTGAGAACAC
TAAACTCTACATCTCCCTTCCCGAGCAAGGAGCTGGCTGAAGCCACAAAAACATTGCTGCATAGT
CTTGGGACTCTGGCCCAGGAGCTGTTCAGCATGAGAAGCTGGAGTGACATGCGACAGGAGGTGAT
GTTTCTGACCAATGTGAACAGCTCCAGCTCCTCCACCCAAATCTACCAGGCTGTGTCTCGTATTG
TCTGCGGGCATCCCGAGGGAGGGGGGCTGAAGATCAAGTCTCTCAACTGGTATGAGGACAACAAC
TACAAAGCCCTCTTTGGAGGCAATGGCACTGAGGAAGATGCTGAAACCTTCTATGACAACTCTAC
AACTCCTTACTGCAATGATTTGATGAAGAATTTGGAGTCTAGTCCTCTTTCCCGCATTATCTGGA
AAGCTCTGAAGCCGCTGCTCGTTGGGAAGATCCTGTATACACCTGACACTCCAGCCACAAGGCAG
GTCATGGCTGAGGTGAACAAGACCTTCCAGGAACTGGCTGTGTTCCATGATCTGGAAGGCATGTG
GGAGGAACTCAGCCCCAAGATCTGGACCTTCATGGAGAACAGCCAAGAAATGGACCTTGTCCGGA
```

FIG. 3

```
TGCTGTTGGACAGCAGGGACAATGACCACTTTTGGGAACAGCAGTTGGATGGCTTAGATTGGACA
GCCCAAGACATCGTGGCGTTTTTGGCCAAGCACCCAGAGGATGTCCAGTCCAGTAATGGTTCTGT
GTACACCTGGAGAGAAGCTTTCAACGAGACTAACCAGGCAATCCGGACCATATCTCGCTTCATGG
AGTGTGTCAACCTGAACAAGCTAGAACCCATAGCAACAGAAGTCTGGCTCATCAACAAGTCCATG
GAGCTGCTGGATGAGAGGAAGTTCTGGGCTGGTATTGTGTTCACTGGAATTACTCCAGGCAGCAT
TGAGCTGCCCCATCATGTCAAGTACAAGATCCGAATGGACATTGACAATGTGGAGAGGACAAATA
AAATCAAGGATGGGTACTGGGACCCTGGTCCTCGAGCTGACCCCTTTGAGGACATGCGGTACGTC
TGGGGGGGCTTCGCCTACTTGCAGGATGTGGTGGAGCAGGCAATCATCAGGGTGCTGACGGGCAC
CGAGAAGAAAACTGGTGTCTATATGCAACAGATGCCCTATCCCTGTTACGTTGATGACATCTTTC
TGCGGGTGATGAGCCGGTCAATGCCCCTCTTCATGACGCTGGCCTGGATTTACTCAGTGGCTGTG
ATCATCAAGGGCATCGTGTATGAGAAGGAGGCACGGCTGAAAGAGACCATGCGGATCATGGGCCT
GGACAACAGCATCCTCTGGTTTAGCTGGTTCATTAGTAGCCTCATTCCTCTTCTTGTGAGCGCTG
GCCTGCTAGTGGTCATCCTGAAGTTAGGAAACCTGCTGCCCTACAGTGATCCCAGCGTGGTGTTT
GTCTTCCTGTCCGTGTTTGCTGTGGTGACAATCCTGCAGTGCTTCCTGATTAGCACACTCTTCTC
CAGAGCCAACCTGGCAGCAGCCTGTGGGGCATCATCTACTTCACGCTGTACCTGCCCTACGTCC
TGTGTGTGGCATGGCAGGACTACGTGGGCTTCACACTCAAGATCTTCGCTAGCCTGCTGTCTCCT
GTGGCTTTTGGGTTTGGCTGTGAGTACTTTGCCCTTTTTGAGGAGCAGGGCATTGGAGTGCAGTG
GGACAACCTGTTTGAGAGTCCTGTGGAGGAAGATGGCTTCAATCTCACCACTTCGGTCTCCATGA
TGCTGTTTGACACCTTCCTCTATGGGGTGATGACCTGGTACATTGAGGCTGTCTTTCCAGGCCAG
TACGGAATTCCCAGGCCCTGGTATTTTCCTTGCACCAAGTCCTACTGGTTTGGCGAGGAAAGTGA
TGAGAAGAGCCACCCTGGTTCCAACCAGAAGAGAATATCAGAAATCTGCATGGAGGAGGAACCCA
CCCACTTGAAGCTGGGCGTGTCCATTCAGAACCTGGTAAAAGTCTACCGAGATGGGATGAAGGTG
GCTGTCGATGGCCTGGCACTGAATTTTTATGAGGGCCAGATCACCTCCTTCCTGGGCCACAATGG
AGCGGGGAAGACGACCACCATGTCAATCCTGACCGGGTTGTTCCCCCCGACCTCGGGCACCGCCT
ACATCCTGGGAAAAGACATTCGCTCTGAGATGAGCACCATCCGGCAGAACCTGGGGGTCTGTCCC
CAGCATAACGTGCTGTTTGACATGCTGACTGTCGAAGAACACATCTGGTTCTATGCCCGCTTGAA
AGGGCTCTCTGAGAAGCACGTGAAGGCGGAGATGGAGCAGATGGCCCTGGATGTTGGTTTGCCAT
CAAGCAAGCTGAAAAGCAAAACAAGCCAGCTGTCAGGTGGAATGCAGAGAAAGCTATCTGTGGCC
TTGGCCTTTGTCGGGGGATCTAAGGTTGTCATTCTGGATGAACCCACAGCTGGTGTGGACCCTTA
CTCCCGCAGGGGAATATGGGAGCTGCTGCTGAAATACCGACAAGGCCGCACCATTATTCTCTCTA
CACACCACATGGATGAAGCGGACGTCCTGGGGGACAGGATTGCCATCATCTCCCATGGGAAGCTG
TGCTGTGTGGGCTCCTCCCTGTTTCTGAAGAACCAGCTGGGAACAGGCTACTACCTGACCTTGGT
CAAGAAAGATGTGGAATCCTCCCTCAGTTCCTGCAGAAACAGTAGTAGCACTGTGTCATACCTGA
AAAAGGAGGACAGTGTTTCTCAGAGCAGTTCTGATGCTGGCCTGGGCAGCGACCATGAGAGTGAC
ACGCTGACCATCGATGTCTCTGCTATCTCCAACCTCATCAGGAAGCATGTGTCTGAAGCCCGGCT
GGTGGAAGACATAGGGCATGAGCTGACCTATGTGCTGCCATATGAAGCTGCTAAGGAGGGAGCCT
TTGTGGAACTCTTTCATGAGATTGATGACCGGCTCTCAGACCTGGGCATTTCTAGTTATGGCATC
TCAGAGACGACCCTGGAAGAAATATTCCTCAAGGTGGCCGAAGAGAGTGGGGTGGATGCTGAGAC
CTCAGATGGTACCTTGCCAGCAAGACGAAACAGGCGGGCCTTCGGGGACAAGCAGAGCTGTCTTC
```

FIG. 3 (cont.)

```
GCCCGTTCACTGAAGATGATGCTGCTGATCCAAATGATTCTGACATAGACCCAGAATCCAGAGAG
ACAGACTTGCTCAGTGGGATGGATGGCAAAGGGTCCTACCAGGTGAAAGGCTGGAAACTTACACA
GCAACAGTTTGTGGCCCTTTTGTGGAAGAGACTGCTAATTGCCAGACGGAGTCGGAAAGGATTTT
TTGCTCAGATTGTCTTGCCAGCTGTGTTTGTCTGCATTGCCCTTGTGTTCAGCCTGATCGTGCCA
CCCTTTGGCAAGTACCCCAGCCTGGAACTTCAGCCCTGGATGTACAACGAACAGTACACATTTGT
CAGCAATGATGCTCCTGAGGACACGGGAACCCTGGAACTCTTAAACGCCCTCACCAAAGACCCTG
GCTTCGGGACCCGCTGTATGGAAGGAAACCCAATCCCAGACACGCCCTGCCAGGCAGGGGAGGAA
GAGTGGACCACTGCCCCAGTTCCCCAGACCATCATGGACCTCTTCCAGAATGGGAACTGGACAAT
GCAGAACCCTTCACCTGCATGCCAGTGTAGCAGCGACAAAATCAAGAAGATGCTGCCTGTGTGTC
CCCCAGGGGCAGGGGGCTGCCTCCTCCACAAAGAAAACAAAACACTGCAGATATCCTTCAGGAC
CTGACAGGAAGAAACATTTCGGATTATCTGGTGAAGACGTATGTGCAGATCATAGCCAAAAGCTT
AAAGAACAAGATCTGGGTGAATGAGTTTAGGTATGGCGGCTTTTCCCTGGGTGTCAGTAATACTC
AAGCACTTCCTCCGAGTCAAGAAGTTAATGATGCCATCAAACAAATGAAGAAACACCTAAAGCTG
GCCAAGGACAGTTCTGCAGATCGATTTCTCAACAGCTTGGGAAGATTTATGACAGGACTGGACAC
CAAAAATAATGTCAAGGTGTGGTTCAATAACAAGGGCTGGCATGCAATCAGCTCTTTCCTGAATG
TCATCAACAATGCCATTCTCCGGGCCAACCTGCAAAAGGGAGAGAACCCTAGCCATTATGGAATT
ACTGCTTTCAATCATCCCCTGAATCTCACCAAGCAGCAGCTCTCAGAGGTGGCTCTGATGACCAC
ATCAGTGGATGTCCTTGTGTCCATCTGTGTCATCTTTGCAATGTCCTTCGTCCCAGCCAGCTTTG
TCGTATTCCTGATCCAGGAGCGGGTCAGCAAAGCAAAACACCTGCAGTTCATCAGTGGAGTGAAG
CCTGTCATCTACTGGCTCTCTAATTTTGTCTGGGATATGTGCAATTACGTTGTCCCTGCCACACT
GGTCATTATCATCTTCATCTGCTTCCAGCAGAAGTCCTATGTGTCCTCCACCAATCTGCCTGTGC
TAGCCCTTCTACTTTTGCTGTATGGGTGGTCAATCACACCTCTCATGTACCCAGCCTCCTTTGTG
TTCAAGATCCCCAGCACAGCCTATGTGGTGCTCACCAGCGTGAACCTCTTCATTGGCATTAATGG
CAGCGTGGCCACCTTTGTGCTGGAGCTGTTCACCGACAATAAGCTGAATAATATCAATGATATCC
TGAAGTCCGTGTTCTTGATCTTCCCACATTTTTGCCTGGGACGAGGGCTCATCGACATGGTGAAA
AACCAGGCAATGGCTGATGCCCTGGAAAGGTTTGGGGAGAATCGCTTTGTGTCACCATTATCTTG
GGACTTGGTGGGACGAAACCTCTTCGCCATGGCCGTGGAAGGGGTGGTGTTCTTCCTCATTACTG
TTCTGATCCAGTACAGATTCTTCATCAGGCCCAGACCTGTAAATGCAAAGCTATCTCCTCTGAAT
GATGAAGATGAAGATGTGAGGCGGGAAAGACAGAGAATTCTTGATGGTGGAGGCCAGAATGACAT
CTTAGAAATCAAGGAGTTGACGAAGATATATAGAAGGAAGCGGAAGCCTGCTGTTGACAGGATTT
GCGTGGGCATTCCTCCTGGTGAGTGCTTTGGGCTCCTGGGAGTTAATGGGGCTGGAAAATCATCA
ACTTTCAAGATGTTAACAGGAGATACCACTGTTACCAGAGGAGATGCTTTCCTTAACAAAAATAG
TATCTTATCAAACATCCATGAAGTACATCAGAACATGGGCTACTGCCCTCAGTTTGATGCCATCA
CAGAGCTGTTGACTGGGAGAGAACACGTGGAGTTCTTTGCCCTTTTGAGAGGAGTCCCAGAGAAA
GAAGTTGGCAAGGTTGGTGAGTGGGCGATTCGGAAACTGGGCCTCGTGAAGTATGGAGAAAAATA
TGCTGGTAACTATAGTGGAGGCAACAAACGCAAGCTCTCTACAGCCATGGCTTTGATCGGCGGGC
CTCCTGTGGTGTTTCTGGATGAACCCACCACAGGCATGGATCCCAAAGCCCGGCGGTTCTTGTGG
AATTGTGCCCTAAGTGTTGTCAAGGAGGGGAGATCAGTAGTGCTTACATCTCATAGTATGGAAGA
ATGTGAAGCTCTTTGCACTAGGATGGCAATCATGGTCAATGGAAGGTTCAGGTGCCTTGGCAGTG
TCCAGCATCTAAAAAATAGGTTTGGAGATGGTTATACAATAGTTGTACGAATAGCAGGGTCCAAC
```

FIG. 3 (cont.)

```
CCGGACCTGAAGCCTGTCCAGGATTTCTTTGGACTTGCATTTCCTGGAAGTGTTCTAAAAGAGAA
ACACCGGAACATGCTACAATACCAGCTTCCATCTTCATTATCTTCTCTGGCCAGGATATTCAGCA
TCCTCTCCCAGAGCAAAAAGCGACTCCACATAGAAGACTACTCTGTTTCTCAGACAACACTTGAC
CAAGTATTTGTGAACTTTGCCAAGGACCAAAGTGATGATGACCACTTAAAAGACCTCTCATTACA
CAAAAACCAGACAGTAGTGGACGTTGCAGTTCTCACATCTTTTCTACAGGATGAGAAAGTGAAAG
AAAGCTATGTAACGCGTACGCGGCCGCTCGAGCAGAAACTCATCTCAGAAGAGGATCTGGCAGCA
AATGATATCCTGGATTACAAGGATGACGACGATAAGGTTTAAACGGCCGGCCGCGGTCATAGCTG
TTTCCTGAACAGATCCCGGGTGGCATCCCTGTGACCCCTCCCCAGTGCCTCTCCTGGCCCTGGAA
GTTGCCACTCCAGTGCCCACCAGCCTTGTCCTAATAAAATTAAGTTGCATCATTTTGTCTGACTA
GGTGTCCTTCTATAATATTATGGGGTGGAGGGGGTGGTATGGAGCAAGGGGCAAGTTGGGAAGA
CAACCTGTAGGGCCTGCGGGGTCTATTGGGAACCAAGCTGGAGTGCAGTGGCACAATCTTGGCTC
ACTGCAATCTCCGCCTCCTGGGTTCAAGCGATTCTCCTGCCTCAGCCTCCCGAGTTGTTGGGATT
CCAGGCATGCATGACCAGGCTCAGCTAATTTTTGTTTTTTTGGTAGAGACGGGGTTTCACCATAT
TGGCCAGGCTGGTCTCCAACTCCTAATCTCAGGTGATCTACCCACCTTGGCCTCCCAAATTGCTG
GGATTACAGGCGTGAACCACTGCTCCCTTCCCTGTCCTTCTGATTTTAAAATAACTATACCAGCA
GGAGGACGTCCAGACACAGCATAGGCTACCTGGCCATGCCCAACCGGTGGGACATTTGAGTTGCT
TGCTTGGCACTGTCCTCTCATGCGTTGGGTCCACTCAGTAGATGCCTGTTGAATTGGGTACGCGG
CCAGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTG
CTGGCGTTTTTCCATAGGCTCCGCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTC
ACGTTAAGGGATTTTGGTCATGAGATTATCAAAAAGGATCTTCACCTAGATCCTTTTAAATTAAA
AATGAAGTTTTAAATCAATCTAAAGTATATATGAGTAACCTGAGGCTATGGCAGGGCCTGCCGCC
CCGACGTTGGCTGCGAGCCCTGGGCCTTCACCCGAACTTGGGGGGTGGGGTGGGAAAAGGAAGA
AACGCGGGCGTATTGGCCCCAATGGGGTCTCGGTGGGGTATCGACAGAGTGCCAGCCCTGGGACC
GAACCCCGCGTTTATGAACAAACGACCCAACACCGTGCGTTTTATTCTGTCTTTTTATTGCCGTC
ATAGCGCGGGTTCCTTCCGGTATTGTCTCCTTCCGTGTTTCAGTTAGCCTCCCCCTAGGGTGGGC
GAAGAACTCCAGCATGAGATCCCCGCGCTGGAGGATCATCCAGCCGGCGTCCCGGAAAACGATTC
CGAAGCCCAACCTTTCATAGAAGGCGGCGGTGGAATCGAAATCTCGTGATGGCAGGTTGGGCGTC
GCTTGGTCGGTCATTTCGAACCCCAGAGTCCCGCTCAGAAGAACTCGTCAAGAAGGCGATAGAAG
GCGATGCGCTGCGAATCGGGAGCGGCGATACCGTAAAGCACGAGGAAGCGGTCAGCCCATTCGCC
GCCAAGCTCTTCAGCAATATCACGGGTAGCCAACGCTATGTCCTGATAGCGATCCGCCACACCCA
GCCGGCCACAGTCGATGAATCCAGAAAAGCGGCCATTTTCCACCATGATATTCGGCAAGCAGGCA
```

FIG. 3 (cont.)

```
TCGCCATGGGTCACGACGAGATCCTCGCCGTCGGGCATGCTCGCCTTGAGCCTGGCGAACAGTTC
GGCTGGCGCGAGCCCCTGATGCTCTTCGTCCAGATCATCCTGATCGACAAGACCGGCTTCCATCC
GAGTACGTGCTCGCTCGATGCGATGTTTCGCTTGGTGGTCGAATGGGCAGGTAGCCGGATCAAGC
GTATGCAGCCGCCGCATTGCATCAGCCATGATGGATACTTTCTCGGCAGGAGCAAGGTGAGATGA
CAGGAGATCCTGCCCCGGCACTTCGCCCAATAGCAGCCAGTCCCTTCCCGCTTCAGTGACAACGT
CGAGCACAGCTGCGCAAGGAACGCCCGTCGTGGCCAGCCACGATAGCCGCGCTGCCTCGTCTTGC
AGTTCATTCAGGGCACCGGACAGGTCGGTCTTGACAAAAAGAACCGGGCGCCCTGCGCTGACAG
CCGGAACACGGCGGCATCAGAGCAGCCGATTGTCTGTTGTGCCCAGTCATAGCCGAATAGCCTCT
CCACCCAAGCGGCCGGAGAACCTGCGTGCAATCCATCTTGTTCAATCATGCGAAACGATCCTCAT
CCTGTCTCTTGATCGATCTTTGCAAAAGCCTAGGCCTCCAAAAAAGCCTCCTCACTACTTCTGGA
ATAGCTCAGAGGCCGAGGCGGCCTCGGCCTCTGCATAAATAAAAAAAATTAGTCAGCCATGGGC
GGAGAATGGGCGGAACTGGGCGGAGTTAGGGGCGGGATGGGCGGAGTTAGGGGCGGGACTATGGT
TGCTGACTAATTGAGATGCATGCTTTGCATACTTCTGCCTGCTGGGGAGCCTGGGGACTTTCCAC
ACCTGGTTGCTGACTAATTGAGATGCATGCTTTGCATACTTCTGCCTGCTGGGGAGCCTGGGGAC
TTTCCACACCCTAACTGACACACATTCCACAGCTGGTTCTTTCCGCCTCAGGACTCTTCCTTTTT
CAATATTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTGACGCGCCCTGTA
GCGGCGCATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTTTCGCCCTTTG
ACGTTGGAGTCCACGTTCTTTAATAGTGGACTCTTGTTCCAAACTGGAACAACACTCAACCCTAT
CTCGGTCTATTCTTTTGATTTATAAGGGATTTTGCCGATTTCGGCCTATTGGTTAAAAAATGAGC
TGATTTAACAAAAATTTAACGCGAATTTTAACAAAATATT
```

FIG. 3 (cont.)

SONOCHEMICAL INDUCTION OF ABCA1 EXPRESSION AND COMPOSITIONS THEREFOR

FIELD OF THE INVENTION

This invention relates to compositions comprising sonochemically-active microspheres and a plasmid encoding ATP-binding cassette transporter A1, and methods of inducing ATP-binding cassette transporter A1 expression in vivo.

SEQUENCE LISTING INCORPORATION

Biological sequence information for this application is included in an ASCII text file having the file name "SG-2-SEQ-4_ST25.txt", created on Sep. 10, 2013 and having a file size of 44617 bytes, which is incorporated herein by reference.

BACKGROUND

High-density lipoprotein (HDL) is the largest of the five major groups of lipoproteins. Other lipoproteins include chylomicrons, very low-density lipoprotein (VLDL), intermediate-density lipoprotein (IDL), and low-density lipoprotein (LDL). HDL and other lipoproteins enable cholesterol and other lipids (e.g., triglycerides) to be transported within the bloodstream, despite their hydrophobic nature. About thirty percent of blood cholesterol is carried by HDL in healthy adults.

ATP-binding cassette transporter A1 (ABCA1) is an integral cell membrane protein that exports excess cholesterol from cells in conjunction with phospholipid that is necessary for the initial lipidation of ApoA1 to form nascent high density lipoprotein cholesterol (HDL-c). ABCA1 deficiency leads to very low plasma levels of HDL-c. In contrast, ABCA1 overexpression reportedly protected C57B1/6 mice from diet-induced atherosclerosis. Increasing ABCA1 transcription by enhancing its regulatory gene control by liver X factor (LXR) has led to the induction of not only HDL biogenesis, but also to an adverse increase in lipogenesis, leading to undesirable hepatic steatosis.

HDL-c is formed in the liver and the intestines by the lipidation of apolipoprotein A1 (apoA1) mediated by the ABCA1 transporter protein. Numerous studies of cultured cells, human HDL deficiencies, and animal models have shown that ABCA1 is a major determinant of plasma HDL levels and a potent atheroprotective factor. The role of ABCA1 in the liver for the formation of plasma HDL is well established, but it has been unclear whether stimulation of ABCA1 production will enhance lipidation and secretion of nascent HDL thereby resulting in an increase in plasma HDL-c levels.

The metabolism of HDL is complex and several factors contribute to the transport of cholesterol from arteries to the liver for excretion or re-use (reverse cholesterol transport). Some key players in reverse cholesterol transport include ABCA1, ABCG1, apoA1, apoE, LXR, Niemann Pick proteins 1 and 2 (NPC 1 and NPC2) sterol regulating element binding protein (SREBP), CD36, acyl cholesterol acyl transferase (ACAT) and scavenger receptor A1 (SRA1). Many of these proteins have been considered as drug targets for enhancing blood HDL-c levels; however, the effects of targeting, enhancing the activity of, or otherwise interfering with the normal activity and expression of any of these individual proteins is unpredictable. High cholesterol also commonly is treated by inhibiting production of cholesterol in the liver (e.g., by inhibiting HMG-CoA reductase) or by inhibiting digestion of fats (e.g., by inhibiting bile acid production).

Plasma HDL-c and LDL-c levels are routinely measured as indicators of systemic atherosclerosis resulting in arterial blockage. HDL can remove cholesterol from within arteries and transport the cholesterol back to the liver for excretion or re-utilization. Individuals with higher levels of HDL-c have a reduced tendency for cardiovascular diseases. Low HDL-c cholesterol levels (less than about 40 mg/dL or about 1 mmol/L) are associated with increased risk of heart disease. In patients with Tangier disease (also known as "familial alpha-lipoprotein deficiency"), a rare inherited disorder, mutations in chromosome 9q31 lead to an inactive form of ABCA1. The inactive ABCA1 leads to severely depressed levels of HDL in the blood. Currently, there is no effective treatment for Tangier disease.

Because of the positive epidemiological correlation between HDL-c levels in the blood and reduced risk of heart disease, as well as the link between HDL and Tangier disease, there is an ongoing need for new methods of increasing blood HDL-c levels. The present application addresses this ongoing need.

SUMMARY OF THE INVENTION

The present invention provides compositions useful for transfecting cells (e.g., liver cells) to express ABCA1. The compositions described herein comprise a pharmaceutically acceptable aqueous carrier containing sonochemically-active microspheres together with a plasmid DNA construct encoding an active form of ABCA1 and at least one promoter for the expression thereof. The sonochemically-active microspheres comprise, consist essentially of, or consist of gas bubbles (e.g., a fluorocarbon gas, such as octafluoropropane or perfluorohexane) encapsulated within protein-containing or lipid-containing shells (e.g., human serum albumin shells). The microspheres are disruptable by exposure to ultrasonic energy (sonication) to release the encapsulated gas.

The following embodiments are provided as illustrative, non-limiting examples of the compositions and methods described herein.

Embodiment 1 comprises a composition useful for transfecting cells comprising a mixture of a plasmid vector encoding an active form of ATP-binding cassette transporter A1 (ABCA1) and sonochemically-active microspheres in a pharmaceutically acceptable aqueous carrier. The vector comprises an expressible open reading frame encoding the active form of ABCA1 and at least one sequence adapted to promote expression of the open reading frame in a mammalian cell. The sonochemically-active microspheres comprise gas bubbles encapsulated within shells comprising a protein, a lipid, or a combination thereof, the microspheres being disruptable upon exposure to ultrasonic acoustic energy to release the encapsulated gas bubbles.

Embodiment 2 comprises the composition of embodiment 1 wherein the microspheres have an average particle size in the range of about 0.5 to about 20 micrometers.

Embodiment 3 comprises the composition of embodiment 1 or embodiment 2 wherein the gas comprises a fluorocarbon gas.

Embodiment 4 comprises the composition of any one of embodiments 1 to 3 wherein the shells comprise human serum albumin.

Embodiment 5 comprises the composition of any one of embodiments 1 to 4 wherein the active form of ABCA1 has the amino acid sequence of SEQ ID NO: 1.

Embodiment 6 comprises the composition of any one of embodiments 1 to 5 wherein the open reading frame has the nucleotide sequence of SEQ ID NO: 2.

Embodiment 7 comprises the composition of any one of embodiments 1 to 6 wherein the at least one sequence adapted to promote expression of the open reading frame comprises a cytomegalovirus promoter.

Embodiment 8 comprises the composition of any one of embodiments 1 to 7 wherein the plasmid is present in the composition at a concentration in the range of about 0.5 to about 50 mg/mL.

Embodiment 9 comprises the composition of any one of embodiments 1 to 8 wherein the microspheres are present in the composition at a concentration in the range of about $10^8$ to about $10^9$ microspheres per milliliter.

Embodiment 10 comprises the composition of any one of embodiments 1 to 9 wherein the aqueous carrier comprises physiological saline, optionally buffered at physiological pH.

Embodiment 11 comprises the composition of any one of embodiments 1 to 10 further comprising at least one material selected from the group consisting of (a) a drug for treating a condition relating to lipid metabolism or transport, (b) a plasmid encoding a protein other than ABCA1 involved in lipid metabolism of transport, and (c) a plasmid encoding an siRNA that targets a protein involved in lipid metabolism or transport.

Embodiment 12 comprises the composition of any one of embodiments 1 to 11 wherein the plasmid encoding ABCA1 also encodes at least one material selected from the group consisting of (a) a protein other than ABCA1 involved in lipid metabolism of transport, and (b) an siRNA that targets a protein involved in lipid metabolism or transport.

Embodiment 13 comprises a composition useful for transfecting cells comprising a mixture of about 0.5 to about 50 mg/mL of a plasmid vector encoding an active form of ATP-binding cassette transporter A1 (ABCA1) and about $10^8$ to about $10^9$ microspheres per milliliter of sonochemically-active microspheres in a pharmaceutically acceptable aqueous carrier; wherein the vector comprises an expressible open reading frame encoding the active form of ABCA1 and at least one sequence adapted to promote expression of the open reading frame in a mammalian cell; and wherein the sonochemically-active microspheres comprise octafluoropropane gas bubbles encapsulated within shells comprising human serum albumin, the microspheres being disruptable upon exposure to ultrasonic acoustic energy to release the encapsulated gas bubbles.

Embodiment 14 comprises a method of transfecting a tissue in vivo to express an active form of ABCA1 in cells of the tissue, the method comprising the steps of (a) intravenously co-administering to a subject a plasmid vector encoding the active form of ATP-binding cassette transporter A1 (ABCA1), and sonochemically-active microspheres; wherein the vector comprises an expressible open reading frame encoding the active form of ABCA1 and at least one sequence adapted to promote expression of the open reading frame in a mammalian cell; and wherein the sonochemically-active microspheres comprise gas bubbles encapsulated within shells comprising a protein, a lipid, or a combination thereof, the microspheres being disruptable upon exposure to ultrasonic acoustic energy to release the encapsulated gas bubbles; (b) ultrasonically imaging the tissue of the subject to be transfected while the plasmid and microspheres of the composition are circulating through the vasculature of the tissue and thereby detecting the presence of the microspheres in the vasculature of the tissue; and (c) while the microspheres are present in the tissue, applying pulses of ultrasonic energy to the tissue at an acoustical energy level higher that that required for imaging and at a sufficient energy level to disrupt the microspheres and release the gas bubbles therefrom, the pulses of ultrasonic energy and release of gas bubbles thereby temporarily increasing the porosity of cells in the tissue to facilitate entry of the plasmid into the cells to effect transfection thereof.

Embodiment 15 comprises the method of embodiment 14 wherein the microspheres have an average particle size in the range of about 0.5 to about 20 micrometers.

Embodiment 16 comprises the method of embodiment 14 or embodiment 15 wherein the gas comprises a fluorocarbon gas.

Embodiment 17 comprises the method of any one of embodiments 14 to 16 wherein the shells comprise human serum albumin.

Embodiment 18 comprises the method of any one of embodiments 14 to 17 wherein the active form of ABCA1 has the amino acid sequence of SEQ ID NO: 1.

Embodiment 19 comprises the method of any one of embodiments 14 to 18 wherein the at least one sequence adapted to promote expression of the open reading frame comprises a cytomegalovirus promoter.

Embodiment 20 comprises the method of any one of embodiments 14 to 19 wherein the plasmid is administered in an aqueous carrier at a concentration in the range of about 0.5 to about 50 mg/mL.

Embodiment 21 comprises the method of any one of embodiments 14 to 20 wherein the microspheres are administered in an aqueous carrier at a concentration in the range of about $10^8$ to about $10^9$ microspheres per milliliter.

Embodiment 22 comprises the method of any one of embodiments 14 to 21 wherein the plasmid and the microspheres are administered as a mixture in one aqueous carrier.

Embodiment 23 comprises the method of any one of embodiments 14 to 21 wherein the plasmid and the microspheres are administered in separate aqueous carriers.

Embodiment 24 comprises the method of any one of embodiments 14 to 23 wherein an additional biologically active agent is co-administered along with the plasmid and microspheres.

Embodiment 25 comprises the method of embodiment 24 wherein the additional biologically active agent comprises at least one material selected from the group consisting of (a) a drug for treating a condition relating to lipid metabolism or transport, (b) a plasmid encoding a protein other than ABCA1 involved in lipid metabolism of transport, and (c) a plasmid encoding an siRNA that targets a protein involved in lipid metabolism or transport.

Embodiment 26 comprises the method of any one of embodiments 14 to 25 wherein the tissue comprises liver tissue, intestinal parenchymal tissue, or a combination thereof. Embodiment 27 comprises use of a composition of any one of embodiments 1 to 13 to enhance high density lipoprotein cholesterol in the blood of a subject (e.g., to treat atherosclerosis).

Embodiment 28 comprises use of a composition of any one of embodiments 1 to 13 for the preparation of a medicament to enhance high density lipoprotein cholesterol in the blood of a subject (e.g., to treat atherosclerosis).

In a study conducted with rats, sonoporation of the liver in conjunction with a peripheral (tail vein) intravenous infusion of an aqueous composition containing ABCA1 plasmids and albumin-encapsulated fluorocarbon gas (octafluoropropane) microspheres resulted in a significant increase in plasma HDL-c levels relative to the baseline HDL-c levels for the rats. In this study, ABCA1 plasmid achieved a higher serum concentration of HDL-c than apoA1 plasmid. This finding is both surprising and novel the current understanding in this field is the most effective method to increase hepatic secretion of HDL-c is to increase apoA1 synthesis. In fact, treatment with both the ABCA1 plasmid and the apoA1 plasmid was no better than an infusion of ABCA1 alone in this study.

BRIEF DESCRIPTION OF THE DRAWINGS

FIG. 1 provides the amino acid sequence of human ABCA1 (SEQ ID NO: 1) utilized in the examples herein.

FIG. 2 provides the open reading frame nucleotide sequence of human ABCA1 (SEQ ID NO: 1) utilized in the examples herein.

FIG. 3 illustrates the nucleotide sequence of the plasmid (SEQ ID NO: 3) utilized in the examples herein.

DETAILED DESCRIPTION OF SELECTED EMBODIMENTS

Figure 4:
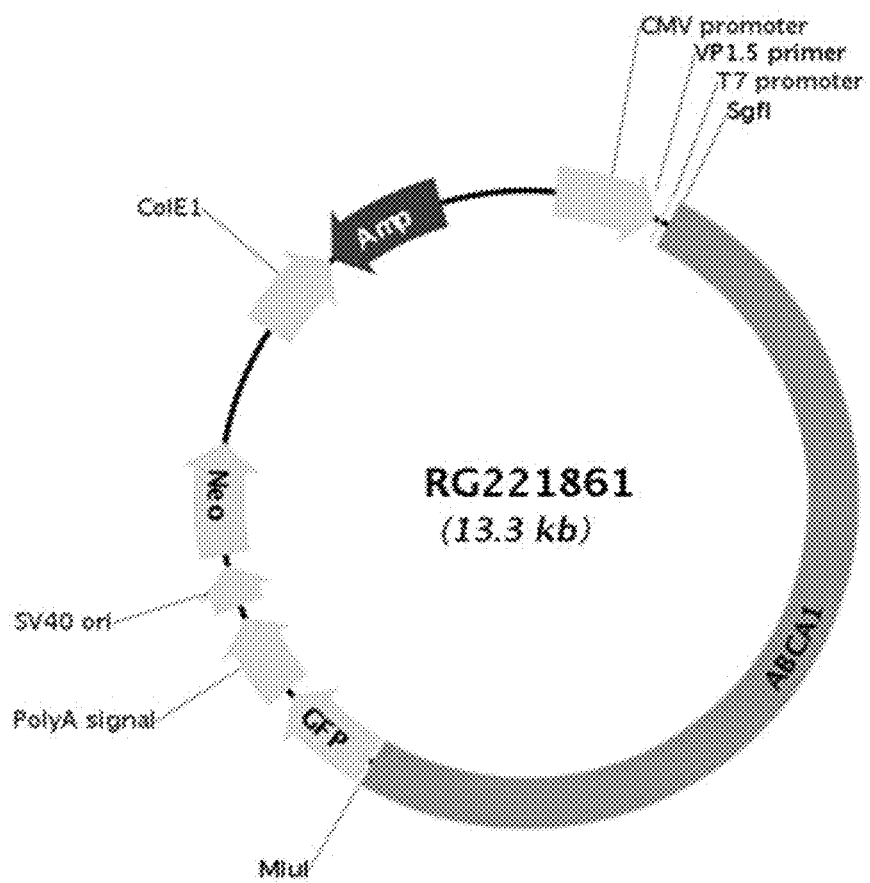
FIG. 4 provides a schematic illustration of the ABCA1 plasmid utilized in the examples described herein.

In one aspect, the present invention provides compositions useful for transfecting cells to express ABCA1 comprise a pharmaceutically acceptable aqueous carrier containing sonochemically-active microspheres together with a plasmid DNA construct encoding an active form of ABCA1 and at least one promoter for the expression thereof. The sonochemically-active microspheres comprise, consist essentially of, or consist of gas bubbles encapsulated within protein-containing or lipid-containing shells. The microspheres are disruptable by sonication (i.e., exposure to ultrasonic acoustic energy), releasing the encapsulated gas.

In another aspect, the present invention provides a method of inducing ABCA1 expression in cells in vivo, and a method enhancing high density lipoprotein cholesterol in the blood. These methods comprise intravenously co-administering an ABCA1 plasmid and sonochemically active microspheres as described herein to a subject, ultrasonically imaging the a target tissue (e.g., the liver or intestinal parenchymal tissue) of the subject to detect when the microspheres are circulating through the vasculature of the tissue. The imaging typically is performed by external application of ultrasonic acoustic energy at a mechanical index (MI; which is defined as the peak negative acoustic pressure divided by the square of the imaging frequency) less than about 0.4 MI. When the microspheres are detected in the target tissue, pulses of ultrasonic acoustic energy are applied to the tissue at an acoustic energy level higher than the energy level needed for imaging (typically greater than 1 MI, preferably greater than 1.3 MI, and up to about 2 MI), and of sufficiently high acoustic energy to disrupt the shells of the microspheres and release the gas bubbles encapsulated by the shells. The pulses preferably are applied at an acoustic frequency of about 1 to about 7 MHz. The acoustic energy of the pulses and the release of gas bubbles in the tissue temporarily increases the porosity of the tissue cell membranes (a process referred to herein as "sonoporation").

Sonoporation of a tissue such as the liver comprises supplying ultrasonic acoustic energy pulses to the tissue with the ultrasound imaging probe. The pulses are applied while ultrasonically imaging the tissue so that the pulses are applied primarily when the microspheres (and thus also the co-administered plasmid) are present. The pulses typically are applied at a rate of about 6 to about 8 pulses per minute for a total of about 5 to about 20 pulses. The pulse duration typically is in the range of about 500 to about 2000 milliseconds per pulse. The acoustic energy pulses disrupt the microspheres and release the encapsulated gas. This disruption, combined with directly supplied acoustic energy makes the cells more porous to the plasmids, so that the plasmids can enter and transfect the cells. Once transfected, the cells transcribe protein via messenger RNA leading to synthesis of active ABCA1, which in turn enhances HDL formation and HDC-c concentration in the blood.

As used herein, the term "co-administration" and grammatical variations thereof, refers to administering two or more materials to the same individual during the same therapeutic session. Such co-administration can involve administering material separately, or together within the same composition. The co-administration can be simultaneous or can be temporally separated. In addition, sites of co-administration can be in the same location or different locations.

As used herein, the term "plasmid" and grammatical variations thereof refers to small circular DNA that is physically separate from, and can replicate independently of, chromosomal DNA within a cell (i.e., in an episome), and which commonly are found as small (e.g., about one thousand to about one million base pairs) circular, double-stranded DNA molecules in bacteria. Artificial plasmids are used as vectors in molecular cloning, serving to drive the replication of recombinant DNA sequences within episomes in the host cells without altering the chromosomal DNA of the host cells.

As used herein, the term "episomally transfected" and grammatical variations thereof refer to non-insertional (non-integrating) transfection with exogenous episomal nucleic acid, such as DNA, siRNA, RNA, or mRNA (e.g. a plasmid or other episomal vector) to produce a cell with unaltered chromosomal DNA, in which the a polypeptide encoded by the episomal DNA is expressed within the target cells (e.g., liver cells) without genomic integration of the exogenous DNA. As used herein, the term "episome" and grammatical variations thereof refers to closed circular DNA molecules that are replicated in the nucleus, and is intended to encompass exogenous plasmids introduced into host cells such as liver cells. Preferably, the plasmid encodes the active form of ABCA1 and also encodes regulatory elements (e.g., a promoter) to facilitate episomal expression of the ABCA1 protein.

As used herein, the term "active form of ABCA1" and grammatical variations thereof refers to the ABCA1 protein of SEQ ID NO: 1 and variations thereof comprising conservative substitutions in SEQ ID NO: 1 and sharing at least about 95 percent sequence identity (e.g., at least about 95, 96, 97, 98, or 99% sequence identity) with SEQ ID NO: 1 and retaining the lysine residues at positions 939 and 1952 of SEQ ID NO: 1.

Percentage values stated herein are on a weight-weight basis (i.e., "weight percent" or "percent by weight") when referring to a concentration, and on a number basis when referring to a quantity or countable number of items, as the context will make evident and unless otherwise specified.

As used herein, a "therapeutically effective dosage" is an amount (e.g., a total of about 0.5 to about 10 mL of a single composition or co-administered compositions comprising about 0.5 to about 50 mg/mL of the ABCA1 plasmid and about $10^8$ to about $10^9$ of the microspheres per milliliter) such that when administered in conjunction with sonication of the liver, the plasmids transfect cells of the tissue to express the nucleic acid, subsequently resulting in enhanced HDL-c level in the blood, or other effects targeted by the therapy. The dosage and number of doses (e.g. single or multiple dose) administered to a subject will vary depending upon a variety of factors, including the route of administration, patient conditions and characteristics (sex, age, body weight, health, size), extent of symptoms, concurrent treatments, frequency of treatment and the effect desired, the concentration of plasmids in the composition, and the like.

Adjustment and manipulation of dosage ranges, as well as in vitro and in vivo methods of determining the therapeutic effectiveness of the composition in an individual, are well within the ability of those of ordinary skill in the medical arts. In some preferred embodiments, the dosage does not exceed about 5 mL of composition over a 10 minute period. Suitable safe dosages of ultrasonic contrast agents provide a useful guideline for use in the methods described herein. Such safe dosages are well known in the art and are documented in literature from ultrasonic contrast agent manufacturers.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Sonochemically-active microspheres suitable for use in the compositions and methods described herein include any protein-based or lipid-based gas-filled microspheres (also known as "microbubbles") that can be used as ultrasonic imaging contrast agents. The microspheres comprise a physiologically acceptable gas (e.g., a non-toxic gas such as nitrogen, air, oxygen, argon, or a fluorocarbon such as octafluoropropane (also known as "perflutren") or perfluorohexane. The shell of the microspheres can comprise a protein (e.g., human serum albumin), a lipid material (e.g., phospholipids, phosphocholine lipids, and polyethoxylates thereof), or a combination thereof. Some lipid-based microspheres may also contain galactose in the shell. Protein-containing microspheres can include relatively small amounts (e.g., less than about 1 percent) of fatty acids (e.g., caprylic acid), amino acids or amino acid derivatives (e.g., N-acyltryptophan), or other formulation aids. The microspheres typically have a mean particle size (i.e., effective mean diameter) in the range of about 1 to about 10 micrometers (preferably about 1 to about 5 micrometers). Preferably, at least about 95% of the microspheres have a diameter of less than about 10 micrometers. The microspheres preferably are present in the composition at a concentration in the range of about $10^8$ to about $10^9$ of the microspheres per milliliter. The compositions described herein preferably are prepared by simple mixing of a microsphere suspension (e.g., as supplied by the manufacturer) with a solution of the plasmid or plasmids that are to be co-administered.

The pharmaceutically active aqueous carrier of the compositions comprises water (e.g., deionized, pyrogen-free water), and preferably includes one or more salts (e.g., sodium chloride, phosphate, citrate, and the like). In some preferred embodiments the aqueous carrier comprises physiological saline (about 0.9 percent NaCl), phosphate buffered saline, and the like. The carrier optionally can include other soluble materials (e.g., dextrose), preservatives, and the like, to provide a solution that is generally sterile, safe, isotonic and compatible with blood. Preferably, the compositions have a physiological pH (e.g., about pH 6.4 to 7.5).

Some preferred microsphere formulations useful in the compositions and methods described herein include the OPTSON brand microspheres (available from GE Healthcare), IMAGENT brand microspheres (developed by Alliance Pharmaceutical), and DEFINITY brand microspheres (available from Lantheus Medical Imaging, Inc.). Preferably, the compositions comprise human serum albumen encapsulated octafluoropropane microspheres, such as OPTISON microspheres.

According the manufacturer, OPTISON microsphere suspensions from GE Healthcare comprise about $5 \times 10^8$ to about $8 \times 10^8$ microspheres per mL of suspension. The microspheres comprise perflutren (octafluoropropane) gas bubbles encapsulated within shells of human serum albumin. The microspheres have a mean particle diameter of about 3 to about 4.5 µm with about 95% of the microspheres having a diameter of less than about 10 µm. The microspheres are suspended in a physiological saline solution (about 0.9 percent by weight NaCl in water). The compositions also can include less than about 1 percent caprylic acid, and less than about 1 percent N-acyltryptophan. Each milliliter of OPTISON microspheres reportedly comprises about 10 mg of human serum albumin, about 0.2 to 0.3 mg of perflutren, about 0.2 mg N-acetyltryptophan, and about 0.12 mg capiylic acid in 0.9% aqueous sodium chloride at a pH of about 6.4-7.4. The headspace of the vial containing the suspension is filled with perflutren gas. The manufacturer recommends that the injection rate should not exceed about 1 mL per second (maximum total dose should not exceed about 5 mL in any 10 minute period, and maximum total dose should not exceed about 8.7 mL in any one patient study).

IMAGENT perflexane lipid microsphere composition (trade name previously IMAVIST) is an injectable suspension developed by Alliance Pharmaceutical. The microspheres reportedly comprise perflexane (perfluorohexane) microbubbles encapsulated in a lipid-based shell comprising 1,2-dimyristoyl-sn-glycero-3-phosphocholine (DMPC), hydroxyethyl starch and poloxomer (a nonionic triblock copolymer composed of a central hydrophobic chain of polyoxypropylene flanked by two hydrophilic chains of polyoxyethylene). The microspheres are suspended in a phosphate buffered saline solution.

According to manufacturer information, DEFINITY perflutren lipid microspheres are provided as an injectable suspension. The DEFINITY material is supplied as components that upon activation yield perflutren lipid microspheres. The material is supplied in a vial containing a clear, colorless, sterile, non-pyrogenic, hypertonic liquid, which upon activation with the aid of a VIALMIX brand activator, provides a homogeneous, opaque, milky white injectable suspension of perflutren lipid microspheres. The suspension of activated DEFINITY microspheres is administered by intravenous injection. The perflutren lipid microspheres are composed of octafluoropropane encapsulated in an outer lipid shell consisting of (R)-hexadecanoic acid-1-[(phosphonoxy)methyl]-1,2-ethanediyl ester, monosodium salt (abbreviated. DPPA);

(R)-4-hydroxy-N,N,N-trimethyl10-oxo-7-[(1-oxohexadecyl)oxy]-3,4,9-trioxa-4-phosphapentacosan-1-aminium-4-oxide inner salt (abbreviated DPPC); and (R)-α-[6-hydroxy-6-oxido-9-[(1-oxohexadecyl)oxy]5,7,11-trioxa-2-aza-6-phosphahexacos-1-yl]-ω-methoxypoly(ox-1,2-ethanediyl), monosodium salt (abbreviated MPEG5000 DPPE).

DPPA has a molecular weight of 670, empirical formula of $C_{35}H_{68}O_8PNa$, and following structural formula:

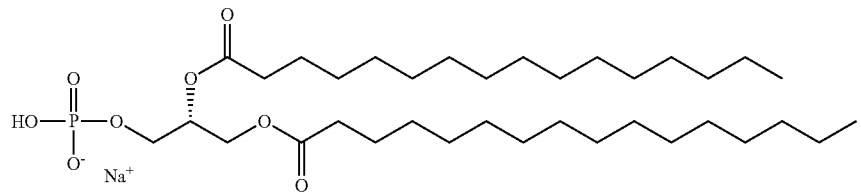 [SMILES: CCCCCCCCCCCCCCCC(=O)OC[C@H](COP(=O)([O-])O)OC(=O)CCCCCCCCCCCCCCC ; [Na+]]

DPPC has a molecular weight of 734, empirical formula of $C_{40}H_{80}NO_8P$, and following structural formula:

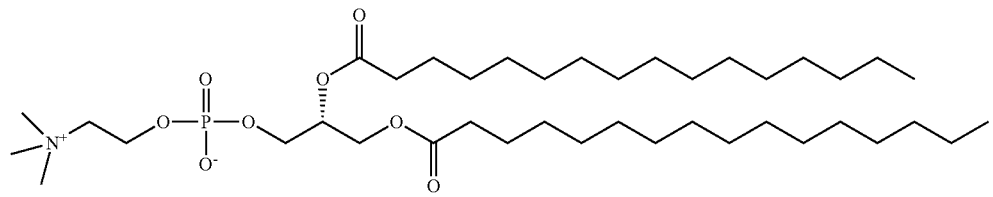 [SMILES: CCCCCCCCCCCCCCCC(=O)OC[C@H](COP(=O)([O-])OCC[N+](C)(C)C)OC(=O)CCCCCCCCCCCCCCC]

MPEG5000 DPPE has an approximate molecular weight of 5750 represented by empirical formula $C_{265}H_{527}NO_{123}PNa$, and the following structural formula:

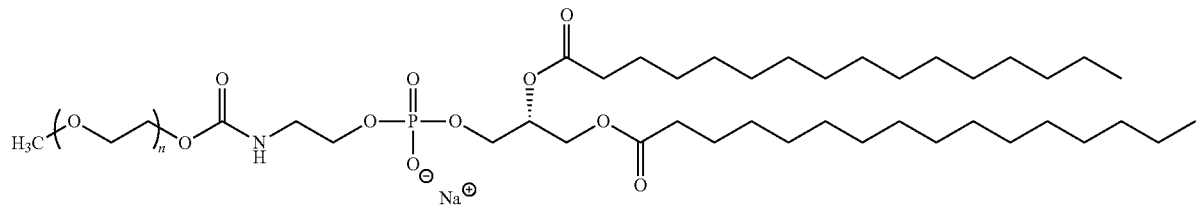

Prior to VIALMIX activation, the DEFINITY component vial reportedly contains 6.52 mg/mL octafluoropropane in the headspace. Each mL of the clear liquid reportedly contains 0.75 mg lipid blend (consisting of 0.045 mg DPPA, 0.401 mg DPPC, and 0.304 mg MPEG5000 DPPE), 103.5 mg propylene glycol, 126.2 mg glycerin, 2.34 mg sodium phosphate monobasic monohydrate, 2.16 mg sodium phosphate dibasic heptahydrate, and 4.87 mg sodium chloride in water (pH is 6.2-6.8). After activating the contents of the vial, each mL of the milky white suspension reportedly contains a maximum of $1.2 \times 10^{10}$ perflutren lipid microspheres, and about 150 µm/mL (1.1 mg/mL) octafluoropropane. The microsphere mean particle size is about 1.1 µm to 3.3 µm, with 98% of the microspheres having a diameter of less than 10 µm.

Plasmid Design.

Plasmids generally comprise a strong viral promoter to drive the in vivo transcription and translation of the encoded gene (or complementary DNA, RNA, siRNA, or mDNA) of interest (which is present as an open reading frame). Intron A may can be included to improve mRNA stability and hence increase protein expression. Plasmids also typically include a strong polyadenylation/transcriptional termination signal, such as bovine growth hormone or rabbit beta-globulin polyadenylation sequences.

Because the plasmid provided the genetic material from which the protein of interest is expressed, optimizing vector design for maximal protein expression is desirable. For example, the codon usage can be adjusted to better conform to eukaryotic cells. Another factor to consider is the choice of promoter. Examples of promoters include the simian virus 40 (SV40) promoter, the Rous Sarcoma Virus (RSV) promoter, and the cytomegalovirus (CMV) promoter. In addition, expression rates can sometimes be improved by inclusion of enhancer sequences, adenovirus tripartite leader (TPL) sequences, or modifications to the polyadenylation and transcriptional termination sequences. Non-limiting examples of episomal plasmid vectors suitable for use as vectors for transfection of liver cells include SV40-based vectors, Epstein-Barr virus-based vectors, papilloma virus-based vectors, BK virus-based vectors, and the like, which are well known in the molecular genetics art.

Non limiting examples of episomal vectors suitable for use as non-integrating vectors for transfection of eukaryotic cells (e.g., primary MSC) include simian virus 40-based vectors, Epstein-Barr virus-based vectors, papilloma virus-based vectors, BK virus-based vectors, and the like, which are well known in the molecular genetics art.

In some embodiments, an additional biologically active agent is co-administered along with the plasmid and microspheres. Such additional biologically active agents include, for examples, a drug for treating a condition relating to lipid metabolism or transport, a plasmid encoding a protein other than ABCA1 involved in lipid metabolism of transport, and a plasmid encoding an siRNA that targets a protein involved in lipid metabolism or transport. Additionally, or alternatively, the plasmid encoding the active ABCA1 can also encode an a protein other than ABCA1 involved in lipid metabolism of transport, or a siRNA that targets a protein involved in lipid metabolism or transport.

Non-limiting examples of drugs for treating a condition relating to lipid metabolism or transport include HMG-CoA inhibitors, such as statins (e.g., atorvastatin, cerivastatin, fluvastatin, lovastatin, mevastatin, pitavastatin, pravastatin, rosuvastatin, simvastatin, and combinations thereof); bile acid inhibitors (e.g., cholestyramine, colestipol, colesevalam, and combinations thereof); fibric acid derivatives (e.g., clofibrate, gemfibrozil, fenofibrate) which may lower LDL-c and raise HDL-c; and niacin.

Examples of proteins involved in lipid metabolism or transport include, e.g., ABCA1, ABCG1, apoA1, apoA2, apoE, LXR, NPC1, NPC2, SREBP, CD36, ACAT, SRA1, and HMG-CoA. Such enzymes or siRNA targeting such proteins may be encoded by a plasmid co-administered with the ABCA1 plasmid, or in some cases can be encoded the same plasmid as the ABCA1.

Co-administration of a drug or a plasmid encoding a lipid metabolism/transport protein or siRNA can have the advantage of tailoring treatment to the specific condition suffered by the patient, by invoking multiple action sites, multiple metabolic targets, or both. For example, the materials to be co-administered can be selected e.g., to HDL-c and lower LDL-c in patients where both types of cholesterol are outside the recommended levels, or to raise HDL-c and lower total triglycerides, etc. In addition, different tissues may be transfected in a given subject, e.g., to target optimal tissues that may be involved in the particular lipid metabolic pathways of interest. For example, one tissue may be transfected to express one protein or siRNA, while a different tissue of the same subject may be transfected to express another protein of siRNA.

The following non-limiting examples are provided to illustrate certain features and aspects of the IP-MSC and methods described herein.

Methods and Procedures.

Male Sprague-Dawley rats (180-250 g) were purchased through Charles River Laboratories, Wilmington, Mass. All animal studies performed in an AAALAC, USDA, and OLAW accredited facility. Rats were housed in sterile cages (Alternative Design Manufacturing & Supply Inc., Siloam Springs, Ark.) and provided ad libitum access to standard commercial feed (Lab Diet; Purina Mills, St. Louis, Mo.) and water. Animals were maintained on a 12-hour:12-hour light:dark cycle, controlled temperature (approximately 24° C.) and controlled humidity (approximately 40%).

ApoA1 DNA Plasmids.

An apoA1 expression plasmid was constructed by subcloning an 804 bp human apoA1 PCR cDNA product into expression vector pMIR0125 (Mirus Bio Corp, Madison, Wis.) containing human apoE hepatic control region (HCR), human ubiquitin C promoter and first intron. The final construct, pMIR0332-HCRUbC-h apoA1 was sequenced and the resulting clone matched the reported human apoA1 sequence. An ABCA1 expression vector was purchased from Origene (ABCA1 (NM 005502) Human cDNA ORF Clone, Cat. No. RC221861). FIG. 1 provides the amino acid sequence of ABCA1 (SEQ ID NO: 1) encoded in the open reading frame of the vector. FIG. 2 provides the nucleotide sequence of the ABCA1 open reading frame (SEQ ID NO: 2) of the vector, while FIG. 3 provides the nucleotide sequence of the entire vector (SEQ ID NO: 3). FIG. 4 provides a schematic map of the ABCA1 plasmid.

Infusion Method.

The plasmids (i.e., apoA1 plasmid, ABCA1 plasmid, or a combination of apoA1 and ABCA1 plasmids) were mixed with commercial OPTISON microsphere suspension for injection. Anesthetic: Inhalable gas mixture of oxygen and 1.5-3.0% isoflurane. A warming bed maintained rat body temperature at 37° C. Tail vein injections were performed using a 26 GA ¾-inch catheter. Mixtures: About 1 mL of OPTISON microspheres was mixed with (1) apoA1 DNA plasmid (approximately 8 mg in 1 mL), or (2) ABCA1 plasmid (approximately 7.3 mg in 1 mL), or (3) a combination of apoA1 and ABCA1 plasmids at the same concentrations per mL as used for the individual plasmids.

Plasmid Volume and Concentration of DNA.

All plasmids alone or in combination were mixed with OPTISON microspheres for about 15 to about 30 seconds prior to injection with a 3 mL injection syringe and then co-administered or co-infused. The infusion rate was manually performed at a timed rate of about 2 to 3 mL/minute and the total infusion duration was about 50 to about 70 seconds.

Ultrasound Equipment and Imaging and Therapeutic Parameters.

A VIVID I brand imaging system (GE Healthcare Systems, Milwaukee, Wis.) equipped with a 3S ultrasound probe was utilized for all liver sonications. All acoustic energy settings remained within FDA guidelines outlined for diagnostic use (ALARA principle). The rat liver was continually visualized using external ultrasound to verify appearance of OPTISON mixture within the liver vasculature and parenchyma. Low mechanical index (MI) ultrasound acoustic energy was used for imaging (e.g., <0.4 MI) whereas, higher MI (about 1.3 MI or greater) was used for therapy. No surgical abdominal incision was ever performed; external ultrasound was used to visualize the liver. The abdomen was shaved to eliminate surface hair.

The ultrasound parameters consisted of an continuous low mechanical index (MI<0.4) ultrasound exposure for "imaging" followed by a two-second "pulse" for therapeutic effect for a total of 10 "pulses." A pulse was defined as a relatively higher (MI>1.3) burst of an ultrasound pulse. In sum, the "pulse" length was about 2 seconds with a pulse interval of about 8 seconds for a total of 10 pulses.

Blood Samples.

Three tail vein blood samples (0.5 ml) were collected over 6 days to establish a baseline serum HDL-c for each rat prior to treatment. After treatment with the plasmids in the OPTISON microsphere suspensions, blood samples were collected daily for three days and then after a three day hiatus. All blood samples were collected in glass test tubes containing a lithium heparin anticoagulant. The separated serum samples were analyzed using a clinical lipid panel test strip (PTS #1710 Lipid Panel Test for CARDIOCHEK PA CHOLESTEROL ANALYZER, Polymer Technology Systems, Inc., Indianapolis, Ind.) to quantify HDL values. Graphical data are reported as mean+1 SEM and statistical significance was determined by a two-sample t-test. The null hypothesis was rejected at P<0.05 and all statistical analyses were carried out using MINITAB12 (Minitab Inc., State College, Pa. USA).

Results.

Figure 5:
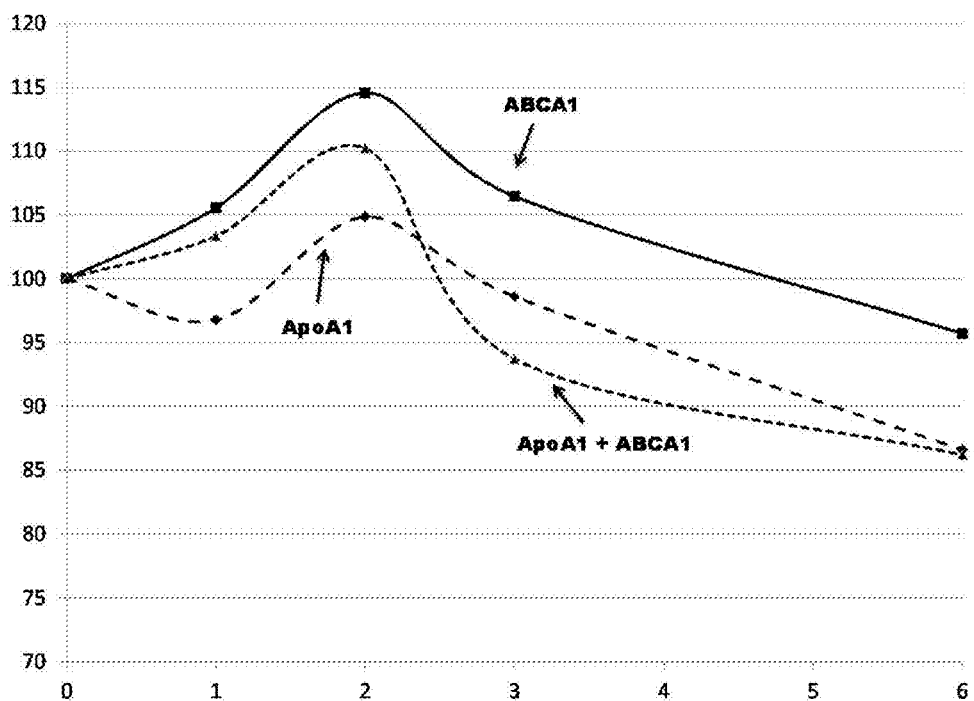
FIG. 5 provides a graph of blood HDL-c in rats following sonochemical treatment with compositions comprising OPTISON microspheres and plasmids encoding ABCA1, apoA1, or a combination thereof.

FIG. 5 provides a graph of blood HDL-c levels of the treated rats, including the baseline level and levels for three days post-treatment. The selective hepatic transduction of ABCA1 through sonoporation described herein resulted in enhanced blood HDL-c relative to baseline HDL-c concentration. A single sonochemical treatment with an ABCA1 plasmid and sonochemically active microsphere composition in conjunction with sonication of the liver resulted in a 15% increase in HDL-c. A surprising finding in this study was that the ABCA1 plasmid therapy resulted in superior increases in HDL-c relative to treatment with an apoA1 plasmid or the combination of ABCA1 and apoA1 plasmids under the same sonication conditions.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A pharmaceutical composition for increasing HDL-cholesterol levels in the blood of a patient, the composition comprising a mixture of a nucleic acid encoding an expressible open reading frame and sonochemically-active microspheres in a pharmaceutically acceptable aqueous carrier; wherein the nucleic acid of the mixture consists of a plasmid vector, the expressible open reading frame consists of an expressible open reading frame encoding the active form of ATP-binding cassette transporter A1 (ABCA1), and the plasmid vector also includes at least one sequence adapted to promote expression of the open reading frame in a mammalian cell; and wherein the sonochemically-active microspheres comprise gas bubbles encapsulated within shells comprising a protein, a lipid, or a combination thereof, the microspheres being disruptable upon exposure to ultrasonic acoustic energy to release the encapsulated gas bubbles; and wherein the composition transfects liver cells when intravenously administered to the patient while ultrasonically imaging the liver, to elicit production of an increased level of HDL-cholesterol in the blood of the patient compared to the HDL-cholesterol level in the blood of the patient prior to administering the composition.

2. The composition of claim 1 wherein the microspheres have an average particle size in the range of about 0.5 to about 20 micrometers.

3. The composition of claim 1 wherein the gas bubbles comprise a fluorocarbon gas.

4. The composition of claim 1 wherein the shells comprise human serum albumin.

5. The composition of claim 1 wherein the active form of ABCA1 has the amino acid sequence of SEQ ID NO: 2.

6. The composition of claim 1 wherein the open reading frame has the nucleotide sequence of SEQ ID NO: 1.

7. The composition of claim 1 wherein the at least one sequence adapted to promote expression of the open reading frame comprises a cytomegalovirus promoter.

8. The composition of claim 1 wherein the plasmid is present in the composition at a concentration in the range of about 0.5 to about 50 milligrams per milliliter.

9. The composition of claim 1 wherein the microspheres are present in the composition at a concentration in the range of about $10^8$ to about $10^9$ microspheres per milliliter.

10. The composition of claim 1 wherein the aqueous carrier comprises physiological saline, optionally buffered at physiological pH.

11. The composition of claim 1 further comprising a drug for treating a condition relating to lipid metabolism or transport.

12. A pharmaceutical composition for increasing HDL-cholesterol levels in the blood of a patient, the composition comprising a mixture of about 0.5 to about 50 milligrams per milliliter of a nucleic acid encoding an expressible open reading frame and about 108 to about 109 microspheres per milliliter of sonochemically-active microspheres in a pharmaceutically acceptable aqueous carrier; wherein the nucleic acid of the mixture consists of a plasmid vector, the expressible open reading frame consists of an expressible open reading frame encoding the active form of ATP-binding cassette transporter A1 (ABCA1), and the plasmid vector also includes at least one sequence adapted to promote expression of the open reading frame in a mammalian cell; and wherein the sonochemically-active microspheres comprise fluorocarbon gas bubbles encapsulated within shells comprising human serum albumin, the microspheres being disruptable upon exposure to ultrasonic acoustic energy to release the encapsulated gas bubbles; and wherein the composition transfects liver cells when intravenously administered to the patient while ultrasonically imaging the liver, to elicit production of an increased level of HDL-cholesterol in the blood of the patient compared to the HDL-cholesterol level in the blood of the patient prior to administering the composition.

13. The composition of claim 12 wherein the active form of ABCA1 has the amino acid sequence of SEQ ID NO: 2.

14. The composition of claim 12 wherein the open reading frame has the nucleotide sequence of SEQ ID NO: 1.

* * * * *

SEQUENCE LISTING

```
<160> NUMBER OF SEQ ID NOS: 3

<210> SEQ ID NO 1
<211> LENGTH: 2261
<212> TYPE: PRT
<213> ORGANISM: Homo sapiens
<220> FEATURE:
<221> NAME/KEY: MISC_FEATURE
<223> OTHER INFORMATION: Human ABCA1

<400> SEQUENCE: 1

Met Ala Cys Trp Pro Gln Leu Arg Leu Leu Leu Trp Lys Asn Leu Thr
1               5                   10                  15

Phe Arg Arg Arg Gln Thr Cys Gln Leu Leu Leu Glu Val Ala Trp Pro
                20                  25                  30

Leu Phe Ile Phe Leu Ile Leu Ile Ser Val Arg Leu Ser Tyr Pro Pro
            35                  40                  45

Tyr Glu Gln His Glu Cys His Phe Pro Asn Lys Ala Met Pro Ser Ala
        50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
                100                 105                 110

Leu Leu Tyr Ser Gln Lys Asp Thr Ser Met Lys Asp Met Arg Lys Val
            115                 120                 125

Leu Arg Thr Leu Gln Gln Ile Lys Lys Ser Ser Ser Asn Leu Lys Leu
        130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
                180                 185                 190

Ser Leu Cys Asn Gly Ser Lys Ser Glu Glu Met Ile Gln Leu Gly Asp
            195                 200                 205

Gln Glu Val Ser Glu Leu Cys Gly Leu Pro Arg Glu Lys Leu Ala Ala
        210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
                260                 265                 270
```

```
Phe Ser Met Arg Ser Trp Ser Asp Met Arg Gln Glu Val Met Phe Leu
            275                 280                 285

Thr Asn Val Asn Ser Ser Ser Ser Thr Gln Ile Tyr Gln Ala Val
290                 295                 300

Ser Arg Ile Val Cys Gly His Pro Glu Gly Gly Leu Lys Ile Lys
305             310              315                 320

Ser Leu Asn Trp Tyr Glu Asp Asn Tyr Lys Ala Leu Phe Gly Gly
                325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
            355                 360                 365

Arg Ile Ile Trp Lys Ala Leu Lys Pro Leu Leu Val Gly Lys Ile Leu
            370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
            435                 440                 445

Trp Glu Gln Gln Leu Asp Gly Leu Asp Trp Thr Ala Gly Asp Ile Val
            450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
                485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
            515                 520                 525

Glu Arg Lys Phe Trp Ala Gly Ile Val Phe Thr Gly Ile Thr Pro Gly
            530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
            595                 600                 605

Thr Gly Thr Glu Lys Lys Thr Gly Val Tyr Met Gln Gln Met Pro Tyr
            610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
            675                 680                 685
```

```
Ser Leu Ile Pro Leu Leu Val Ser Ala Gly Leu Leu Val Ile Leu
    690                 695                 700

Lys Leu Gly Asn Leu Leu Pro Tyr Ser Asp Pro Ser Val Phe Val
705                 710                 715                 720

Phe Leu Ser Val Phe Ala Val Val Thr Ile Leu Gln Cys Phe Leu Ile
                725                 730                 735

Ser Thr Leu Phe Ser Arg Ala Asn Leu Ala Ala Ala Cys Gly Gly Ile
            740                 745                 750

Ile Tyr Phe Thr Leu Tyr Leu Pro Tyr Val Leu Cys Val Ala Trp Gln
        755                 760                 765

Asp Tyr Val Gly Phe Thr Leu Lys Ile Phe Ala Ser Leu Leu Ser Pro
770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Val Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Met Ser
930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                 1000                1005

Lys Ala Glu Met Glu Gln Met Ala Leu Asp Val Gly Leu Pro Ser
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065

Arg Gly Ile Trp Glu Leu Leu Lys Tyr Arg Gln Gly Arg Thr
    1070                1075                1080

Ile Ile Leu Ser Thr His His Met Asp Glu Ala Asp Val Leu Gly
    1085                1090                1095
```

```
Asp Arg Ile Ala Ile Ile Ser His Gly Lys Leu Cys Cys Val Gly
    1100                1105                1110
Ser Ser Leu Phe Leu Lys Asn Gln Leu Gly Thr Gly Tyr Tyr Leu
    1115                1120                1125
Thr Leu Val Lys Lys Asp Val Glu Ser Ser Leu Ser Ser Cys Arg
    1130                1135                1140
Asn Ser Ser Ser Thr Val Ser Tyr Leu Lys Lys Glu Asp Ser Val
    1145                1150                1155
Ser Gln Ser Ser Ser Asp Ala Gly Leu Gly Ser Asp His Glu Ser
    1160                1165                1170
Asp Thr Leu Thr Ile Asp Val Ser Ala Ile Ser Asn Leu Ile Arg
    1175                1180                1185
Lys His Val Ser Glu Ala Arg Leu Val Glu Asp Ile Gly His Glu
    1190                1195                1200
Leu Thr Tyr Val Leu Pro Tyr Glu Ala Ala Lys Glu Gly Ala Phe
    1205                1210                1215
Val Glu Leu Phe His Glu Ile Asp Asp Arg Leu Ser Asp Leu Gly
    1220                1225                1230
Ile Ser Ser Tyr Gly Ile Ser Glu Thr Thr Leu Glu Glu Ile Phe
    1235                1240                1245
Leu Lys Val Ala Glu Glu Ser Gly Val Asp Ala Glu Thr Ser Asp
    1250                1255                1260
Gly Thr Leu Pro Ala Arg Arg Asn Arg Arg Ala Phe Gly Asp Lys
    1265                1270                1275
Gln Ser Cys Leu Arg Pro Phe Thr Glu Asp Asp Ala Ala Asp Pro
    1280                1285                1290
Asn Asp Ser Asp Ile Asp Pro Glu Ser Arg Glu Thr Asp Leu Leu
    1295                1300                1305
Ser Gly Met Asp Gly Lys Gly Ser Tyr Gln Val Lys Gly Trp Lys
    1310                1315                1320
Leu Thr Gln Gln Gln Phe Val Ala Leu Leu Trp Lys Arg Leu Leu
    1325                1330                1335
Ile Ala Arg Arg Ser Arg Lys Gly Phe Phe Ala Gln Ile Val Leu
    1340                1345                1350
Pro Ala Val Phe Val Cys Ile Ala Leu Val Phe Ser Leu Ile Val
    1355                1360                1365
Pro Pro Phe Gly Lys Tyr Pro Ser Leu Glu Leu Gln Pro Trp Met
    1370                1375                1380
Tyr Asn Glu Gln Tyr Thr Phe Val Ser Asn Asp Ala Pro Glu Asp
    1385                1390                1395
Thr Gly Thr Leu Glu Leu Leu Asn Ala Leu Thr Lys Asp Pro Gly
    1400                1405                1410
Phe Gly Thr Arg Cys Met Glu Gly Asn Pro Ile Pro Asp Thr Pro
    1415                1420                1425
Cys Gln Ala Gly Glu Glu Glu Trp Thr Thr Ala Pro Val Pro Gln
    1430                1435                1440
Thr Ile Met Asp Leu Phe Gln Asn Gly Asn Trp Thr Met Gln Asn
    1445                1450                1455
Pro Ser Pro Ala Cys Gln Cys Ser Ser Asp Lys Ile Lys Lys Met
    1460                1465                1470
Leu Pro Val Cys Pro Pro Gly Ala Gly Gly Leu Pro Pro Pro Gln
    1475                1480                1485
```

```
Arg Lys Gln Asn Thr Ala Asp Ile Leu Gln Asp Leu Thr Gly Arg
1490            1495                1500

Asn Ile Ser Asp Tyr Leu Val Lys Thr Tyr Val Gln Ile Ile Ala
1505            1510                1515

Lys Ser Leu Lys Asn Lys Ile Trp Val Asn Glu Phe Arg Tyr Gly
1520            1525                1530

Gly Phe Ser Leu Gly Val Ser Asn Thr Gln Ala Leu Pro Pro Ser
1535            1540                1545

Gln Glu Val Asn Asp Ala Ile Lys Gln Met Lys Lys His Leu Lys
1550            1555                1560

Leu Ala Lys Asp Ser Ser Ala Asp Arg Phe Leu Asn Ser Leu Gly
1565            1570                1575

Arg Phe Met Thr Gly Leu Asp Thr Lys Asn Asn Val Lys Val Trp
1580            1585                1590

Phe Asn Asn Lys Gly Trp His Ala Ile Ser Ser Phe Leu Asn Val
1595            1600                1605

Ile Asn Asn Ala Ile Leu Arg Ala Asn Leu Gln Lys Gly Glu Asn
1610            1615                1620

Pro Ser His Tyr Gly Ile Thr Ala Phe Asn His Pro Leu Asn Leu
1625            1630                1635

Thr Lys Gln Gln Leu Ser Glu Val Ala Leu Met Thr Thr Ser Val
1640            1645                1650

Asp Val Leu Val Ser Ile Cys Val Ile Phe Ala Met Ser Phe Val
1655            1660                1665

Pro Ala Ser Phe Val Val Phe Leu Ile Gln Glu Arg Val Ser Lys
1670            1675                1680

Ala Lys His Leu Gln Phe Ile Ser Gly Val Lys Pro Val Ile Tyr
1685            1690                1695

Trp Leu Ser Asn Phe Val Trp Asp Met Cys Asn Tyr Val Val Pro
1700            1705                1710

Ala Thr Leu Val Ile Ile Ile Phe Ile Cys Phe Gln Gln Lys Ser
1715            1720                1725

Tyr Val Ser Ser Thr Asn Leu Pro Val Leu Ala Leu Leu Leu Leu
1730            1735                1740

Leu Tyr Gly Trp Ser Ile Thr Pro Leu Met Tyr Pro Ala Ser Phe
1745            1750                1755

Val Phe Lys Ile Pro Ser Thr Ala Tyr Val Val Leu Thr Ser Val
1760            1765                1770

Asn Leu Phe Ile Gly Ile Asn Gly Ser Val Ala Thr Phe Val Leu
1775            1780                1785

Glu Leu Phe Thr Asp Asn Lys Leu Asn Asn Ile Asn Asp Ile Leu
1790            1795                1800

Lys Ser Val Phe Leu Ile Phe Pro His Phe Cys Leu Gly Arg Gly
1805            1810                1815

Leu Ile Asp Met Val Lys Asn Gln Ala Met Ala Asp Ala Leu Glu
1820            1825                1830

Arg Phe Gly Glu Asn Arg Phe Val Ser Pro Leu Ser Trp Asp Leu
1835            1840                1845

Val Gly Arg Asn Leu Phe Ala Met Ala Val Glu Gly Val Val Phe
1850            1855                1860

Phe Leu Ile Thr Val Leu Ile Gln Tyr Arg Phe Phe Ile Arg Pro
1865            1870                1875
```

-continued

```
Arg Pro Val Asn Ala Lys Leu Ser Pro Leu Asn Asp Glu Asp Glu
    1880            1885            1890

Asp Val Arg Arg Glu Arg Gln Arg Ile Leu Asp Gly Gly Gly Gln
    1895            1900            1905

Asn Asp Ile Leu Glu Ile Lys Glu Leu Thr Lys Ile Tyr Arg Arg
    1910            1915            1920

Lys Arg Lys Pro Ala Val Asp Arg Ile Cys Val Gly Ile Pro Pro
    1925            1930            1935

Gly Glu Cys Phe Gly Leu Leu Gly Val Asn Gly Ala Gly Lys Ser
    1940            1945            1950

Ser Thr Phe Lys Met Leu Thr Gly Asp Thr Thr Val Thr Arg Gly
    1955            1960            1965

Asp Ala Phe Leu Asn Lys Asn Ser Ile Leu Ser Asn Ile His Glu
    1970            1975            1980

Val His Gln Asn Met Gly Tyr Cys Pro Gln Phe Asp Ala Ile Thr
    1985            1990            1995

Glu Leu Leu Thr Gly Arg Glu His Val Glu Phe Phe Ala Leu Leu
    2000            2005            2010

Arg Gly Val Pro Glu Lys Glu Val Gly Lys Val Gly Glu Trp Ala
    2015            2020            2025

Ile Arg Lys Leu Gly Leu Val Lys Tyr Gly Glu Lys Tyr Ala Gly
    2030            2035            2040

Asn Tyr Ser Gly Gly Asn Lys Arg Lys Leu Ser Thr Ala Met Ala
    2045            2050            2055

Leu Ile Gly Gly Pro Pro Val Val Phe Leu Asp Glu Pro Thr Thr
    2060            2065            2070

Gly Met Asp Pro Lys Ala Arg Arg Phe Leu Trp Asn Cys Ala Leu
    2075            2080            2085

Ser Val Val Lys Glu Gly Arg Ser Val Val Leu Thr Ser His Ser
    2090            2095            2100

Met Glu Glu Cys Glu Ala Leu Cys Thr Arg Met Ala Ile Met Val
    2105            2110            2115

Asn Gly Arg Phe Arg Cys Leu Gly Ser Val Gln His Leu Lys Asn
    2120            2125            2130

Arg Phe Gly Asp Gly Tyr Thr Ile Val Val Arg Ile Ala Gly Ser
    2135            2140            2145

Asn Pro Asp Leu Lys Pro Val Gln Asp Phe Phe Gly Leu Ala Phe
    2150            2155            2160

Pro Gly Ser Val Leu Lys Glu Lys His Arg Asn Met Leu Gln Tyr
    2165            2170            2175

Gln Leu Pro Ser Ser Leu Ser Leu Ala Arg Ile Phe Ser Ile
    2180            2185            2190

Leu Ser Gln Ser Lys Lys Arg Leu His Ile Glu Asp Tyr Ser Val
    2195            2200            2205

Ser Gln Thr Thr Leu Asp Gln Val Phe Val Asn Phe Ala Lys Asp
    2210            2215            2220

Gln Ser Asp Asp Asp His Leu Lys Asp Leu Ser Leu His Lys Asn
    2225            2230            2235

Gln Thr Val Val Asp Val Ala Val Leu Thr Ser Phe Leu Gln Asp
    2240            2245            2250

Glu Lys Val Lys Glu Ser Tyr Val
    2255            2260
```

-continued

```
<210> SEQ ID NO 2
<211> LENGTH: 6783
<212> TYPE: DNA
<213> ORGANISM: Artificial Sequence
<220> FEATURE:
<223> OTHER INFORMATION: ABCA1 Open Reading Frame
<220> FEATURE:
<221> NAME/KEY: misc_feature
<223> OTHER INFORMATION: ABCA1 Open Reading Frame

<400> SEQUENCE: 2
atggcttgtt ggcctcagct gaggttgctg ctgtggaaga acctcacttt cagaagaaga      60
caaacatgtc agctgctgct ggaagtggcc tggcctctat ttatcttcct gatcctgatc     120
tctgttcggc tgagctaccc accctatgaa caacatgaat gccattttcc aaataaagcc     180
atgccctctg caggaacact tccttgggtt caggggatta tctgtaatgc caacaacccc     240
tgtttccgtt acccgactcc tggggaggct cccggagttg ttggaaactt aacaaatcc      300
attgtggctc gcctgttctc agatgctcgg aggcttcttt tatacagcca gaaagacacc     360
agcatgaagg acatgcgcaa agttctgaga acattacagc agatcaagaa atccagctca     420
aacttgaagc ttcaagattt cctggtggac aatgaaacct ctctgggtt cctgtatcac      480
aacctctctc tcccaaagtc tactgtggac aagatgctga gggctgatgt cattctccac     540
aaggtatttt gcaaggcta ccagttacat ttgacaagtc tgtgcaatgg atcaaaatca      600
gaagagatga ttcaacttgg tgaccaagaa gtttctgagc tttgtggcct accaggggag     660
aaactggctg cagcagagcg agtacttcgt tccaacatgg acatcctgaa gccaatcctg     720
agaacactaa actctacatc tcccttcccg agcaaggagc tggctgaagc cacaaaaaca     780
ttgctgcata gtcttggac tctggcccag gagctgttca gcatgagaag ctggagtgac     840
atgcgacagg aggtgatgtt tctgaccaat gtgaacagct ccagctcctc acccaaatc     900
taccaggctg tgtctcgtat tgtctgcggg catcccgagg gagggggct gaagatcaag     960
tctctcaact ggtatgagga caacaactac aaagccctct ttggaggcaa tggcactgag    1020
gaagatgctg aaaccttcta tgacaactct acaactcctt actgcaatga tttgatgaag    1080
aatttggagt ctagtcctct ttcccgcatt atctggaaag ctctgaagcc gctgctcgtt    1140
gggaagatcc tgtatacacc tgacactcca gccacaaggc aggtcatggc tgaggtgaac    1200
aagaccttcc aggaactggc tgtgttccat gatctggaag gcatgtggga ggaactcagc    1260
cccaagatct ggaccttcat ggagaacagc caagaaatgg accttgtccg gatgctgttg    1320
gacagcaggg acaatgacca cttttgggaa cagcagttgg atggcttaga ttggacagcc    1380
caagacatcg tggcgttttt ggccaagcac ccagaggatg tccagtccag taatggttct    1440
gtgtacacct ggagagaagc tttcaacgag actaaccagg caatccggac catatctcgc    1500
ttcatggagt gtgtcaacct gaacaagcta gaacccatag aacagaagt ctggctcatc    1560
aacaagtcca tggagctgct ggatgagagg aagttctggg ctggtattgt gttcactgga    1620
attactccag gcagcattga gctgccccat catgtcaagt acaagatccg aatggacatt    1680
gacaatgtgg agaggacaaa taaaatcaag gatgggtact gggaccctgg tcctcgagct    1740
gaccccttg aggacatgcg gtacgtctgg ggggcttcg cctacttgca ggatgtggtg    1800
gagcaggcaa tcatcagggt gctgacgggc accgagaaga aaactggtgt ctatatgcaa    1860
cagatgccct atccctgtta cgttgatgac atctttctgc gggtgatgag ccggtcaatg    1920
ccctcttca tgcgctggc ctggatttac tcagtggctg tgatcatcaa gggcatcgtg    1980
tatgagaagg aggcacggct gaaagagacc atgcggatca tgggcctgga caacagcatc    2040
```

-continued

```
ctctggttta gctggttcat tagtagcctc attcctcttc ttgtgagcgc tggcctgcta    2100
gtggtcatcc tgaagttagg aaacctgctg ccctacagtg atcccagcgt ggtgtttgtc    2160
ttcctgtccg tgtttgctgt ggtgacaatc ctgcagtgct tcctgattag cacactcttc    2220
tccagagcca acctggcagc agcctgtggg ggcatcatct acttcacgct gtacctgccc    2280
tacgtcctgt gtgtggcatg gcaggactac gtgggcttca cactcaagat cttcgctagc    2340
ctgctgtctc ctgtggcttt tgggtttggc tgtgagtact ttgccctttt tgaggagcag    2400
ggcattggag tgcagtggga caacctgttt gagagtcctg tggaggaaga tggcttcaat    2460
ctcaccactt cggtctccat gatgctgttt gacaccttcc tctatggggt gatgacctgg    2520
tacattgagg ctgtctttcc aggccagtac ggaattccca ggccctggta ttttccttgc    2580
accaagtcct actggtttgg cgaggaaagt gatgagaaga gccaccctgg ttccaaccag    2640
aagagaatat cagaaatctg catggaggag gaacccaccc acttgaagct gggcgtgtcc    2700
attcagaacc tggtaaaagt ctaccgagat gggatgaagg tggctgtcga tggcctggca    2760
ctgaattttt atgagggcca gatcacctcc ttcctgggcc acaatggagc ggggaagacg    2820
accaccatgt caatcctgac cgggttgttc ccccgacct cgggcaccgc ctacatcctg    2880
ggaaaagaca ttcgctctga gatgagcacc atccggcaga acctgggggt ctgtccccag    2940
cataacgtgc tgtttgacat gctgactgtc gaagaacaca tctggttcta tgcccgcttg    3000
aaagggctct ctgagaagca cgtgaaggcg gagatgagc agatggccct ggatgttggt    3060
ttgccatcaa gcaagctgaa aagcaaaaca agccagctgt caggtggaat gcagagaaag    3120
ctatctgtgg ccttggcctt tgtcggggga tctaaggttg tcattctgga tgaacccaca    3180
gctggtgtgg acccttactc ccgcagggga atatgggagc tgctgctgaa ataccgacaa    3240
ggccgcacca ttattctctc tacacaccac atggatgaag cggacgtcct gggggacagg    3300
attgccatca tctcccatgg gaagctgtgc tgtgtgggct cctccctgtt tctgaagaac    3360
cagctgggaa caggctacta cctgaccttg gtcaagaaag atgtggaatc ctcccctcagt    3420 tcctgcagaa acagtagtag cactgtgtca tacctgaaaa aggaggacag tgtttctcag    3480
agcagttctg atgctggcct gggcagcgac catgagagtg acacgctgac catcgatgtc    3540
tctgctatct ccaacctcat caggaagcat gtgtctgaag cccggctggt ggaagacata    3600
gggcatgagc tgacctatgt gctgccatat aagctgctaa aggagggagc ctttgtggaa    3660
ctctttcatg agattgatga ccggctctca gacctgggca tttctagtta tggcatctca    3720
gagacgaccc tggaagaaat attcctcaag gtggccgaag agagtggggt ggatgctgag    3780
acctcagatg gtaccttgcc agcaagacga acaggcgggg ccttcgggga caagcagagc    3840
tgtcttcgcc cgttcactga agatgatgct gctgatccaa atgattctga catagaccca    3900
gaatccagag agacagactt gctcagtggg atggatggca aagggtccta ccaggtgaaa    3960
ggctggaaac ttacacagca acagtttgtg gcccttttgt ggaagagact gctaattgcc    4020
agacggagtc ggaaaggatt ttttgctcag attgtcttgc cagctgtgtt tgtctgcatt    4080
gcccttgtgt tcagcctgat cgtgccaccc tttggcaagt accccagcct ggaacttcag    4140
ccctggatgc acaacgaaca gtacacattt gtcagcaatg atgctcctga ggacacggga    4200
accctggaac tcttaaacgc cctcaccaaa gaccctggct cgggacccg ctgtatggaa    4260 ggaaacccaa tccagacac gccctgccag gcaggggagg aagagtggac cactgcccca    4320
gttccccaga ccatcatgga cctcttccag aatgggaact ggacaatgca gaacccttca    4380
cctgcatgcc agtgtagcag cgacaaaatc aagaagatgc tgcctgtgtg tccccagggg    4440
```

-continued

```
gcagggggc tgcctcctcc acaaagaaaa caaaacactg cagatatcct tcaggacctg    4500
acaggaagaa acatttcgga ttatctggtg aagacgtatg tgcagatcat agccaaaagc    4560
ttaaagaaca agatctgggt gaatgagttt aggtatggcg gcttttccct gggtgtcagt    4620
aatactcaag cacttcctcc gagtcaagaa gttaatgatg ccatcaaaca aatgaagaaa    4680
cacctaaagc tggccaagga cagttctgca gatcgatttc tcaacagctt gggaagattt    4740
atgacaggac tggacaccaa aaataatgtc aaggtgtggt tcaataacaa gggctggcat    4800
gcaatcagct ctttcctgaa tgtcatcaac aatgccattc tccgggccaa cctgcaaaag    4860
ggagagaacc ctagccatta tggaattact gctttcaatc atcccctgaa tctcaccaag    4920
cagcagctct cagaggtggc tctgatgacc acatcagtgg atgtccttgt gtccatctgt    4980
gtcatctttg caatgtcctt cgtcccagcc agctttgtcg tattcctgat ccaggagcgg    5040
gtcagcaaag caaacacct gcagttcatc agtggagtga agcctgtcat ctactggctc    5100
tctaattttg tctgggatat gtgcaattac gttgtccctg ccacactggt cattatcatc    5160
ttcatctgct tccagcagaa gtcctatgtg tcctccacca atctgcctgt gctagcccttt   5220 ctacttttgc tgtatgggtg gtcaatcaca cctctcatgt acccagcctc ctttgtgttc    5280
aagatcccca gcacagccta tgtggtgctc accagcgtga acctcttcat ggcattaat    5340 ggcagcgtgg ccacctttgt gctggagctg ttcaccgaca ataagctgaa taatatcaat    5400
gatatcctga agtccgtgtt cttgatcttc ccacattttt gcctgggacg agggctcatc    5460
gacatggtga aaaccaggc aatggctgat gccctggaaa ggtttgggga aatcgctttt    5520
gtgtcaccat tatcttggga cttggtggga cgaaacctct cgccatggc cgtggaaggg    5580 gtggtgttct tcctcattac tgttctgatc cagtacagat tcttcatcag gcccagacct    5640
gtaaatgcaa agctatctcc tctgaatgat gaagatgaag atgtgaggcg ggaaagacag    5700
agaattcttg atggtggagg ccagaatgac atcttagaaa tcaaggagtt gacgaagata    5760
tatagaagga agcggaagcc tgctgttgac aggatttgcg tgggcattcc tcctggtgag    5820
tgctttgggc tcctgggagt taatggggct ggaaaatcat caactttcaa gatgttaaca    5880
ggagatacca ctgttaccag aggagatgct ttccttaaca aaaatagtat cttatcaaac    5940
atccatgaag tacatcagaa catgggctac tgccctcagt ttgatgccat cacagagctg    6000
ttgactggga gagaacacgt ggagttcttt gccctttga gaggagtccc agagaaagaa    6060
gttggcaagg ttggtgagtg ggcgattcgg aaactgggcc tcgtgaagta tggagaaaaa    6120
tatgctggta actatagtgg aggcaacaaa cgcaagctct ctacagccat ggctttgatc    6180
ggcgggcctc ctgtggtgtt tctggatgaa cccaccacag gcatggatcc caaagcccgg    6240
cggttcttgt ggaattgtgc cctaagtgtt gtcaaggagg ggagatcagt agtgcttaca    6300
tctcatagta tggaagaatg tgaagctctt tgcactagga tggcaatcat ggtcaatgga    6360
aggttcaggt gccttggcag tgtccagcat ctaaaaaata ggtttggaga tggttataca    6420
atagttgtac gaatagcagg gtccaacccg gacctgaagc ctgtccagga tttctttgga    6480
cttgcatttc ctggaagtgt tctaaaagag aaacaccgga acatgctaca ataccagctt    6540
ccatcttcat tatcttctct ggccaggata ttcagcatcc tctcccagag caaaagcga    6600 ctccacatag aagactactc tgtttctcag acaacacttg accaagtatt tgtgaacttt    6660
gccaaggacc aaagtgatga tgaccactta aagaccctct cattacacaa aaaccagaca    6720
gtagtggacg ttgcagttct cacatctttt ctacaggatg agaaagtgaa agaaagctat    6780
gta                                                                  6783
```

<210> SEQ ID NO 3
<211> LENGTH: 11675
<212> TYPE: DNA
<213> ORGANISM: Artificial Sequence
<220> FEATURE:
<223> OTHER INFORMATION: ABCA1 plasmid
<220> FEATURE:
<221> NAME/KEY: misc_feature
<223> OTHER INFORMATION: ABCA1 plasmid

<400> SEQUENCE: 3

| | | | | | |
|---|---|---|---|---|---|
| aacaaaatat | taacgcttac | aatttccatt | cgccattcag | gctgcgcaac | tgttgggaag | 60 |
| ggcgatcggt | gcgggcctct | tcgctattac | gccagctggc | gaaagggggga | tgtgctgcaa | 120 |
| ggcgattaag | ttgggtaacg | ccagggtttt | cccagtcacg | acgttgtaaa | acgacggcca | 180 |
| gtgccaagct | gatctataca | ttgaatcaat | attggcaatt | agccatatta | gtcattggtt | 240 |
| atatagcata | aatcaatatt | ggctattggc | cattgcatac | gttgtatcta | tatcataata | 300 |
| tgtacattta | tattggctca | gtccaatat | gaccgccatg | ttgacattga | ttattgacta | 360 |
| gttattaata | gtaatcaatt | acgggtcat | tagttcatag | cccatatatg | gagttccgcg | 420 |
| ttacataact | tacggtaaat | ggcccgcctg | gctgaccgcc | caacgacccc | cgcccattga | 480 |
| cgtcaataat | gacgtatgtt | cccatagtaa | cgccaatagg | gactttccat | tgacgtcaat | 540 |
| gggtggagta | tttacggtaa | actgcccact | tggcagtaca | tcaagtgtat | catatgccaa | 600 |
| gtccgccccc | tattgacgtc | aatgacggta | aatggcccgc | ctggcattat | gcccagtaca | 660 |
| tgaccttacg | ggactttcct | acttggcagt | acatctacgt | attagtcatc | gctattacca | 720 |
| tggtgatgcg | gttttggcag | tacaccaatg | ggcgtggata | gcggtttgac | tcacggggat | 780 |
| ttccaagtct | ccacccccatt | gacgtcaatg | ggagtttgtt | ttggcaccaa | aatcaacggg | 840 |
| actttccaaa | atgtcgtaat | aaccccgccc | cgttgacgca | aatgggcggt | aggcgtgtac | 900 |
| ggtgggaggt | ctatataagc | agagctcgtt | tagtgaaccg | tcagaatttt | gtaatacgac | 960 |
| tcactatagg | gcgccggga | attcgtcgac | tggatccggt | accgaggaga | tctgccgccg | 1020 |
| cgatcgccat | ggcttgttgg | cctcagctga | ggttgctgct | gtggaagaac | ctcactttca | 1080 |
| gaagaagaca | acatgtcag | ctgctgctgg | aagtggcctg | gcctctattt | atcttcctga | 1140 |
| tcctgatctc | tgttcggctg | agctacccac | cctatgaaca | acatgaatgc | cattttccaa | 1200 |
| ataaagccat | gccctctgca | ggaacacttc | cttgggttca | ggggattatc | tgtaatgcca | 1260 |
| acaaccctg | tttccgttac | ccgactcctg | ggaggctcc | cggagttgtt | ggaaacttta | 1320 |
| acaaatccat | tgtggctcgc | ctgttctcag | atgctcggag | gcttcttta | tacagccaga | 1380 |
| aagacaccag | catgaaggac | atgcgcaaag | ttctgagaac | attacagcag | atcaagaaat | 1440 |
| ccagctcaaa | cttgaagctt | caagatttcc | tggtggacaa | tgaaaccttc | tctgggttcc | 1500 |
| tgtatcacaa | cctctctctc | ccaaagtcta | ctgtggacaa | gatgctgagg | gctgatgtca | 1560 |
| ttctccacaa | ggtatttttg | caaggctacc | agttacattt | gacaagtctg | tgcaatggat | 1620 |
| caaaatcaga | agagatgatt | caacttggtg | accaagaagt | ttctgagctt | tgtggcctac | 1680 |
| caagggagaa | actggctgca | gcagagcgag | tacttcgttc | caacatggac | atcctgaagc | 1740 |
| caatcctgag | aacactaaac | tctacatctc | ccttcccgag | caaggagctg | gctgaagcca | 1800 |
| caaaaacatt | gctgcatagt | cttgggactc | tggcccagga | gctgttcagc | atgagaagct | 1860 |
| ggagtgacat | gcgacaggag | gtgatgtttc | tgaccaatgt | gaacagctcc | agctcctcca | 1920 |
| cccaaatctca | ccaggctgtg | tctcgtattg | tctgcgggca | tcccgaggga | ggggggctga | 1980 |
| agatcaagtc | tctcaactgg | tatgaggaca | acaactacaa | agcctctctt | ggaggcaatg | 2040 |

```
gcactgagga agatgctgaa accttctatg acaactctac aactccttac tgcaatgatt    2100
tgatgaagaa tttggagtct agtcctcttt cccgcattat ctggaaagct ctgaagccgc    2160
tgctcgttgg gaagatcctg tatacacctg acactccagc cacaaggcag tcatggctg     2220 aggtgaacaa gaccttccag gaactggctg tgttccatga tctggaaggc atgtgggagg    2280
aactcagccc caagatctgg accttcatgg agaacagcca agaaatggac cttgtccgga    2340
tgctgttgga cagcagggac aatgaccact tttgggaaca gcagttggat ggcttagatt    2400
ggacagccca agacatcgtg gcgttttttgg ccaagcaccc agaggatgtc cagtccagta   2460
atggttctgt gtacacctgg agagaagctt caacgagac taaccaggca atccggacca    2520
tatctcgctt catggagtgt gtcaacctga caagctaga acccatagca acagaagtct    2580
ggctcatcaa caagtccatg gagctgctgg atgagaggaa gttctgggct ggtattgtgt    2640
tcactggaat tactccaggc agcattgagc tgccccatca tgtcaagtac aagatccgaa    2700
tggacattga caatgtggag aggacaaata aaatcaagga tgggtactgg gaccctggtc    2760
ctcgagctga ccccttttgag gacatgcggt acgtctgggg gggcttcgcc tacttgcagg    2820
atgtggtgga gcaggcaatc atcagggtgc tgacgggcac cgagaagaaa actggtgtct    2880
atatgcaaca gatgccctat ccctgttacg ttgatgacat ctttctgcgg gtgatgagcc    2940
ggtcaatgcc cctcttcatg acgctggcct ggatttactc agtggctgtg atcatcaagg    3000
gcatcgtgta tgagaaggag gcacggctga agagaccat gcggatcatg ggcctggaca    3060
acagcatcct ctggtttagc tggttcatta gtagcctcat tcctcttctt gtgagcgctg    3120
gcctgctagt ggtcatcctg aagttaggaa acctgctgcc ctacagtgat cccagcgtgg    3180
tgtttgtctt cctgtccgtg tttgctgtgg tgacaatcct gcagtgcttc ctgattagca    3240
cactcttctc cagagccaac ctggcagcag cctgtggggg catcatctac ttcacgctgt    3300
acctgcccta cgtcctgtgt gtggcatggc aggactacgt gggcttcaca ctcaagatct    3360
tcgctagcct gctgtctcct gtggcttttg ggtttggctg tgagtacttt gcccttttttg    3420 aggagcaggg cattggagtg cagtgggaca acctgtttga gagtcctgtg gaggaagatg    3480
gcttcaatct caccacttcg gtctccatga tgctgttttga caccttcctc tatgggtgaa    3540
tgacctggta cattgaggct gtcttttccag gccagtacgg aattcccagg ccctggtatt    3600
ttccttgcac caagtcctac tggttttggcg aggaaagtga tgagaagagc cacctggtt    3660 ccaaccagaa gagaatatca gaaatctgca tggaggagga acccacccac ttgaagctgg    3720
gcgtgtccat tcagaacctg gtaaaagtct accgagatgg gatgaaggtg gctgtcgatg    3780
gcctggcact gaattttttat gagggccaga tcacctcctt cctgggccac aatggagcgg    3840
ggaagacgac caccatgtca atcctgaccg ggttgttccc cccgacctcg ggcaccgcct    3900
acatcctggg aaaagacatt cgctctgaga tgagcaccat ccggcagaac ctgggggtct    3960
gtccccagca taacgtgctg tttgacatgc tgactgtcga agaacacatc tggttctatg    4020
cccgcttgaa agggctctct gagaagcacg tgaaggcgga gatggagcag atggcctgg    4080 atgttggttt gccatcaagc aagctgaaaa gcaaaacaag ccagctgtca ggtggaatgc    4140
agagaaagct atctgtggcc ttggcctttg tcggggatc taaggttgtc attctggatg    4200
aacccacagc tggtgtggac ccttactccc gcagggaat atgggagctg ctgctgaaat    4260
accgacaagg ccgcaccatt attctctcta cacaccacat ggatgaagcg gacgtcctgg    4320
gggacaggat tgccatcatc tcccatggga agctgtgctg tgtgggctcc tccctgtttc    4380
tgaagaacca gctgggaaca ggctactacc tgaccttggt caagaaagat gtggaatcct    4440
```

```
ccctcagttc ctgcagaaac agtagtagca ctgtgtcata cctgaaaaag gaggacagtg    4500
tttctcagag cagttctgat gctggcctgg gcagcgacca tgagagtgac acgctgacca    4560
tcgatgtctc tgctatctcc aacctcatca ggaagcatgt gtctgaagcc cggctggtgg    4620
aagacatagg gcatgagctg acctatgtgc tgccatatga agctgctaag gagggagcct    4680
ttgtggaact cttcatgag attgatgacc ggctctcaga cctgggcatt tctagttatg    4740
gcatctcaga gacgaccctg gaagaaatat tcctcaaggt ggccgaagag agtggggtgg    4800
atgctgagac ctcagatggt accttgccag caagacgaaa caggcgggcc ttcggggaca    4860
agcagagctg tcttcgcccg ttcactgaag atgatgctgc tgatccaaat gattctgaca    4920
tagacccaga atccagagag acagacttgc tcagtgggat ggatggcaaa gggtcctacc    4980
aggtgaaagg ctggaaactt acacagcaac agtttgtggc ccttttgtgg aagagactgc    5040
taattgccag acggagtcgg aaaggatttt ttgctcagat tgtcttgcca gctgtgtttg    5100
tctgcattgc ccttgtgttc agcctgatcg tgccaccctt tggcaagtac cccagcctgg    5160
aacttcagcc ctggatgtac aacgaacagt acacatttgt cagcaatgat gctcctgagg    5220
acacgggaac cctggaactc ttaaacgccc tcaccaaaga ccctggcttc gggacccgct    5280
gtatggaagg aaacccaatc ccagacacgc cctgccaggc aggggaggaa gagtggacca    5340
ctgccccagt tccccagacc atcatggacc tcttccagaa tgggaactgg acaatgcaga    5400
acccttcacc tgcatgccag tgtagcagcg acaaaatcaa gaagatgctg cctgtgtgtc    5460
ccccaggggc agggggctg cctcctccac aaagaaaaca aaacactgca gatatccttc    5520
aggacctgac aggaagaaac atttcggatt atctggtgaa gacgtatgtg cagatcatag    5580
ccaaaagctt aaagaacaag atctgggtga atgagtttag gtatggcggc ttttccctgg    5640
gtgtcagtaa tactcaagca cttcctccga gtcaagaagt taatgatgcc atcaaacaaa    5700
tgaagaaaca cctaaagctg gccaaggaca gttctgcaga tcgatttctc aacagcttgg    5760
gaagatttat gacaggactg gacaccaaaa ataatgtcaa ggtgtggttc aataacaagg    5820
gctggcatgc aatcagctct ttcctgaatg tcatcaacaa tgccattctc cgggccaacc    5880
tgcaaagggg agagaaccct agccattatg gaattactgc tttcaatcat cccctgaatc    5940
tcaccaagca gcagctctca gaggtggctc tgatgaccac atcagtggat gtccttgtgt    6000
ccatctgtgt catctttgca atgtccttcg tcccagccag cttttgtcgta ttcctgatcc    6060
aggagcgggt cagcaaagca aaacacctgc agttcatcag tggagtgaag cctgtcatct    6120
actggctctc taattttgtc tgggatatgt gcaattacgt tgtccctgcc acactggtca    6180
ttatcatctt catctgcttc cagcagaagt cctatgtgtc ctccaccaat ctgcctgtgc    6240
tagcccttct acttttgctg tatgggtggt caatcacacc tctcatgtac ccagcctcct    6300
ttgtgttcaa gatccccagc acagcctatg tggtgctcac cagcgtgaac ctcttcattg    6360
gcattaatgg cagcgtggcc accttttgtgc tggagctgtt caccgacaat aagctgaata    6420
atatcaatga tatcctgaag tccgtgttct tgatcttccc acatttttgc ctgggacgag    6480
ggctcatcga catggtgaaa aaccaggcaa tggctgatgc cctggaaagg tttgggaga    6540
atcgctttgt gtcaccatta tcttgggact ggtgggacg aaacctcttc gccatggccg    6600
tggaagggt ggtgttcttc ctcattactg ttctgatcca gtacagattc ttcatcaggc    6660
ccagacctgt aaatgcaaag ctatctcctc tgaatgatga agatgaagat gtgaggcggg    6720
aaagacagag aattcttgat ggtggaggcc agaatgacat cttagaaatc aaggagttga    6780
cgaagatata tagaaggaag cggaagcctg ctgttgacag gatttgcgtg ggcattcctc    6840
```

```
ctggtgagtg ctttgggctc ctgggagtta atggggctgg aaaatcatca actttcaaga    6900
tgttaacagg agataccact gttaccagag gagatgcttt ccttaacaaa aatagtatct    6960
tatcaaacat ccatgaagta catcagaaca tgggctactg ccctcagttt gatgccatca    7020
cagagctgtt gactgggaga gaacacgtgg agttctttgc cctttgaga ggagtcccag      7080 agaaagaagt tggcaaggtt ggtgagtggg cgattcggaa actgggcctc gtgaagtatg    7140
gagaaaaata tgctggtaac tatagtggag gcaacaaacg caagctctct acagccatgg    7200
ctttgatcgg cgggcctcct gtggtgtttc tggatgaacc caccacaggc atggatccca    7260
aagcccggcg gttcttgtgg aattgtgccc taagtgttgt caaggagggg agatcagtag    7320
tgcttacatc tcatagtatg gaagaatgtg aagctctttg cactaggatg gcaatcatgg    7380
tcaatggaag gttcaggtgc cttggcagtg tccagcatct aaaaaatagg tttggagatg    7440
gttatacaat agttgtacga atagcagggt ccaacccgga cctgaagcct gtccaggatt    7500
tctttggact tgcatttcct ggaagtgttc taaaagagaa acaccggaac atgctacaat    7560
accagcttcc atcttcatta tcttctctgg ccaggatatt cagcatcctc tcccagagca    7620
aaaagcgact ccacatagaa gactactctg tttctcagac aacacttgac caagtatttg    7680
tgaactttgc caaggaccaa agtgatgatg accacttaaa agacctctca ttacacaaaa    7740
accagacagt agtggacgtt gcagttctca catcttttct acaggatgag aaagtgaaag    7800
aaagctatgt aacgcgtacg cggccgctcg agcagaaact catctcagaa gaggatctgg    7860
cagcaaatga tatcctggat tacaaggatg acgacgataa ggtttaaacg gccggccgcg    7920
gtcatagctg tttcctgaac agatcccggg tggcatccct gtgaccctc cccagtgcct     7980 ctcctggccc tggaagttgc cactccagtg cccaccagcc ttgtcctaat aaaattaagt    8040
tgcatcattt tgtctgacta ggtgtccttc tataatatta tggggtggag gggggtggta    8100
tggagcaagg ggcaagttgg gaagacaacc tgtagggcct gcggggtcta ttgggaacca    8160
agctggagtg cagtggcaca atcttggctc actgcaatct ccgcctcctg ggttcaagcg    8220
attctcctgc ctcagcctcc cgagttgttg ggattccagg catgcatgac caggctcagc    8280
taatttttgt ttttttggta gagacggggt ttcaccatat tggccaggct ggtctccaac    8340
tcctaatctc aggtgatcta cccaccttgg cctcccaaat tgctgggatt acaggcgtga    8400
accactgctc ccttccctgt ccttctgatt ttaaaataac tataccagca ggaggacgtc    8460
cagacacagc ataggctacc tggccatgcc caaccggtgg gacatttgag ttgcttgctt    8520
ggcactgtcc tctcatgcgt tgggtccact cagtagatgc ctgttgaatt gggtacgcgg    8580
ccagcggcga gcggtatcag ctcactcaaa ggcggtaata cggttatcca cagaatcagg    8640
ggataacgca ggaaagaaca tgtgagcaaa aggccagcaa aaggccagga accgtaaaaa    8700
ggccgcgttg ctggcgtttt tccataggct ccgcccccct gacgagcatc acaaaaatcg    8760
acgctcaagt cagaggtggc gaaacccgac aggactataa agataccagg cgtttccccc    8820
tggaagctcc ctcgtgcgct ctcctgttcc gaccctgccg cttaccggat acctgtccgc    8880
ctttctccct tcgggaagcg tggcgctttc tcatagctca cgctgtaggt atctcagttc    8940
ggtgtaggtc gttcgctcca agctgggctg tgtgcacgaa ccccccgttc agcccgaccg    9000
ctgcgcctta tccggtaact atcgtcttga gtccaacccg gtaagacacg acttatcgcc    9060
actggcagca gccactggta acaggattag cagagcgagg tatgtaggcg gtgctacaga    9120
gttcttgaag tggtggccta actacggcta cactagaaga acagtatttg gtatctgcgc    9180
tctgctgaag ccagttacct tcggaaaaag agttggtagc tcttgatccg gcaaacaaac    9240
```

```
caccgctggt agcggtggtt tttttgtttg caagcagcag attacgcgca gaaaaaaagg    9300
atctcaagaa gatcctttga tcttttctac ggggtctgac gctcagtgga acgaaaactc    9360
acgttaaggg attttggtca tgagattatc aaaaaggatc ttcacctaga tccttttaaa    9420
ttaaaaatga agttttaaat caatctaaag tatatatgag taacctgagg ctatggcagg    9480
gcctgccgcc ccgacgttgg ctgcgagccc tgggccttca cccgaacttg ggggtgggg    9540 tggggaaaag gaagaaacgc gggcgtattg gccccaatgg ggtctcggtg gggtatcgac    9600
agagtgccag ccctgggacc gaaccccgcg tttatgaaca aacgacccaa caccgtgcgt    9660
tttattctgt cttttttattg ccgtcatagc gcgggttcct tccggtattg tctccttccg    9720
tgtttcagtt agcctccccc tagggtgggc gaagaactcc agcatgagat ccccgcgctg    9780
gaggatcatc cagccggcgt cccggaaaac gattccgaag cccaaccttt catagaaggc    9840
ggcggtggaa tcgaaatctc gtgatggcag gttgggcgtc gcttggtcgg tcatttcgaa    9900
ccccagagtc ccgctcagaa gaactcgtca agaaggcgat agaaggcgat gcgctgcgaa    9960
tcgggagcgg cgataccgta agcacgagg aagcggtcag cccattcgcc gccaagctct   10020
tcagcaatat cacgggtagc caacgctatg tcctgatagc gatccgccac acccagccgg   10080
ccacagtcga tgaatccaga aaagcggcca ttttccacca tgatattcgg caagcaggca   10140
tcgccatggg tcacgacgag atcctcgccg tcgggcatgc tcgccttgag cctggcgaac   10200
agttcggctg cgcgagccc ctgatgctct tcgtccagat catcctgatc gacaagaccg   10260
gcttccatcc gagtacgtgc tcgctcgatg cgatgtttcg cttggtggtc gaatgggcag   10320
gtagccggat caagcgtatg cagccgccgc attgcatcag ccatgatgga tactttctcg   10380
gcaggagcaa ggtgagatga caggagatcc tgccccggca cttcgcccaa tagcagccag   10440
tcccttcccg cttcagtgac aacgtcgagc acagctgcgc aaggaacgcc cgtcgtggcc   10500
agccacgata gccgcgctgc ctcgtcttgc agttcattca gggcaccgga caggtcggtc   10560
ttgacaaaaa gaaccgggcg cccctgcgct gacagccgga acacggcggc atcagagcag   10620
ccgattgtct gttgtgccca gtcatagccg aatagcctct ccacccaagc ggccggagaa   10680
cctgcgtgca atccatcttg ttcaatcatg cgaaacgatc ctcatcctgt ctcttgatcg   10740
atctttgcaa aagcctaggc ctccaaaaaa gcctcctcac tacttctgga atagctcaga   10800
ggccgaggcg gcctcggcct ctgcataaat aaaaaaaatt agtcagccat ggggcggaga   10860
atgggcggaa ctgggcggag ttaggggcgg gatgggcgga gttaggggcg ggactatggt   10920
tgctgactaa ttgagatgca tgctttgcat acttctgcct gctggggagc ctggggactt   10980
tccacacctg gttgctgact aattgagatg catgctttgc atacttctgc ctgctgggga   11040
gcctggggac tttccacacc ctaactgaca cacattccac agctggttct tccgcctca   11100 ggactcttcc ttttttcaata ttattgaagc atttatcagg gttattgtct catgagcgga   11160
tacatatttg aatgtattta gaaaaataaa caaataggg ttccgcgcac atttccccga   11220
aaagtgccac ctgacgcgcc ctgtagcggc gcattaagcg cggcgggtgt ggtggttacg   11280
cgcagcgtga ccgctacact tgccagcgcc ctagcgcccg ctcctttcgc tttcttccct   11340
tcctttctcg ccacgttcgc cggctttccc cgtcaagctc taaatcgggg gctccctta   11400 gggttccgat ttagtgcttt acggcacctc gaccccaaaa aacttgatta gggtgatggt   11460
tcacgtagtg ggccatcgcc ctgatagacg ttttttcgcc ctttgacgtt ggagtccacg   11520
ttctttaata gtggactctt gttccaaact ggaacaacac tcaaccctat ctcggtctat   11580
```

-continued

```
tcttttgatt tataagggat tttgccgatt tcggcctatt ggttaaaaaa tgagctgatt    11640
taacaaaaat ttaacgcgaa ttttaacaaa atatt                               11675
```